US005985621A

United States Patent [19]
Usman et al.

[11] Patent Number: 5,985,621
[45] Date of Patent: *Nov. 16, 1999

[54] 2'-DEOXY-2'-ALKYLNUCLEOTIDE CONTAINING NUCLEIC ACID

[75] Inventors: Nassim Usman, Boulder; Alexander Karpeisky, Lafayette; Leonid Beigelman, Longmont; Anil Modak, Boulder, all of Colo.

[73] Assignee: Ribozyme Pharmaceuticals, Inc., San Diego, Calif.

[*] Notice: This patent is subject to a terminal disclaimer.

[21] Appl. No.: 08/710,113

[22] Filed: Sep. 12, 1996

Related U.S. Application Data

[63] Continuation of application No. 08/218,934, Mar. 29, 1994, Pat. No. 5,639,647.
[51] Int. Cl.$^6$ .............................. C12P 19/34; C12N 9/22; C07H 21/00
[52] U.S. Cl. .................... 435/91.31; 435/199; 536/24.1; 536/24.5; 536/25.1
[58] Field of Search .................................. 435/199, 91.1, 435/91.31; 536/23.1, 24.1, 24.5, 25.1

[56] References Cited

U.S. PATENT DOCUMENTS

| 4,987,071 | 1/1991 | Cech et al. | 435/91.31 |
|---|---|---|---|
| 5,180,818 | 1/1993 | Cech et al. | 536/23.1 |
| 5,639,647 | 6/1997 | Usman et al. | 435/199 |

FOREIGN PATENT DOCUMENTS

| 0519463 | 12/1992 | European Pat. Off. . |
|---|---|---|
| 9207065 | 9/1991 | WIPO . |
| 9315187 | 8/1993 | WIPO . |
| 9402595 | 2/1994 | WIPO . |

OTHER PUBLICATIONS

Ballantyne et al., "Nucleotide sequence of the cDNA for murine intercellular adhesion molecule–1 (ICAM–1)," *Nucleic Acids Research* 17:5853 (1989).

Barinaga, "Ribozymes: Killing the Messenger," *Science* 262:1512–1514 (1993).

Bjergarde et al., "Solid Phase Synthesis of Oligodeoxyribonucleoside phosphorodithioates from thiophosphoramidites," *Nucleic Acids Research* 21:58453–5850 (1991).

Brink et al., "2–C–Nitromethyl and 2–C–Aminomethyl Derivatives of D–Ribose. Preparation of 2'–C–Nitromethyluridines," *J.C.S. Perkin I* 1608–1612 (1977).

Cotten, "The in vivo application of ribozymes," *TIBTECH* 8:174–178 (1990).

Edgington, "Ribozymes: Stop Making Sense," *Biotechnology* 10:256–262 (1992).

Guerrier–Takada, et al., "The RNA Moiety of Ribonuclease P Is the Catalytic Subunit of the Enzyme," *Cell* 35:849–857 (1983).

Hampel and Tritz, "RNA Catalytic Properties of the Minimum (–)s TRSV Sequence," *Biochemistry* 28:4929–4933 (1989).

Hampel et al., "Hairpin Catalytic RNA Model: Evidence for Helices and Sequence Requirement for Substrate RNA," *Nucleic Acids Research* 18:299–304 (1990).

Jeffries and Symons, "A Catalytic 13–mer Ribozyme," *Nucleic Acids Research* 17:1371–1377 (1989).

Kita et al., "Sequence and expression of rat ICAM–1," *Biochem. Biophys. Acta* 1131:108–110 (1992).

Perreault et al., "Mixed Deoxyribo–and Ribo–Oligonucleotides with Catalytic Activity," *Nature* 344:565–567 (1990).

Perrotta and Been, "Cleavage of Oligoribonucleotides by a Ribozyme Derived from the Hepatitis δ Virus RNA Sequence," *Biochemistry* 31:16–21 (1992).

Pieken et al., "Kinetic Characterization of Ribonuclease–Resistant 2'–Modified Hammerhead Ribozymes," *Science* 253:314–317 (1991).

Rossi et al., "Ribozymes as Anti–HIV–1 Therapeutic Agents: Principles, Applications, and Problems," *Aids Research and Human Retroviruses* 8:183–189 (1992).

Simmons et al., "ICAM, an adhesion ligand of LFA–1, is homologous to the neural cell adhesion molecule NCAM," *Nature* 331:624–627 (1988).

Sproat et al., "New Synthetic routes to synthons suitable for 2'–O–allyloligoribonucleotide assembly," *Nucleic Acids Research* 19:733–738 (1991).

Sproat et al., "2'–O–Alkyloligoribonucleotides: Synthesis and Applications in Studying RNA Splicing," *Nucleosides &Nucleotides* 10:25–36 (1991).

Sproat et al., "New synthetic routes to protected purine 2'–O'methylriboside–3'–O–phosphoramidites using a novel alkylation procedure," *Nucleic Acids Research* 18:41–49 (1990).

Stein et al., "Physicochemical properties of phosphorothioate oligodeoxynucleotides," *Nucleic Acids Research* 16:3209–3221 (1988).

Tseng et al., "A Ring–Enlarged Oxetanocin A Analogue as an Inhibitor of HIV Infectivity," *J. Med. Chem.* 34:343–349 (1991).

Uhlenbeck, "A Small Catalytic Oligoribonucleotide," *Nature* 328:596–600 (1987).

Usman and Cedergren, "Exploiting the chemical synthesis of RNA," *TIBS* 17:334–339 (1992).

Xi et al., "New Stereocontrolled Synthesis of Isomeric C–Branched–β–D–Nucleosides by Intramolecular Free–radical Cyclization–Opening Reactions Based on Temporary Silicon Connection," *Tetrahedron* 48:349–370 (1992).

*Primary Examiner*—David Guzo
*Attorney, Agent, or Firm*—Lyon & Lyon LLP

[57] ABSTRACT

2'-deoxy-2'-alkylnucleotides useful for stabilizing enzymatic nucleic acid molecules and antisense molecules.

12 Claims, 11 Drawing Sheets

FIG. 1.

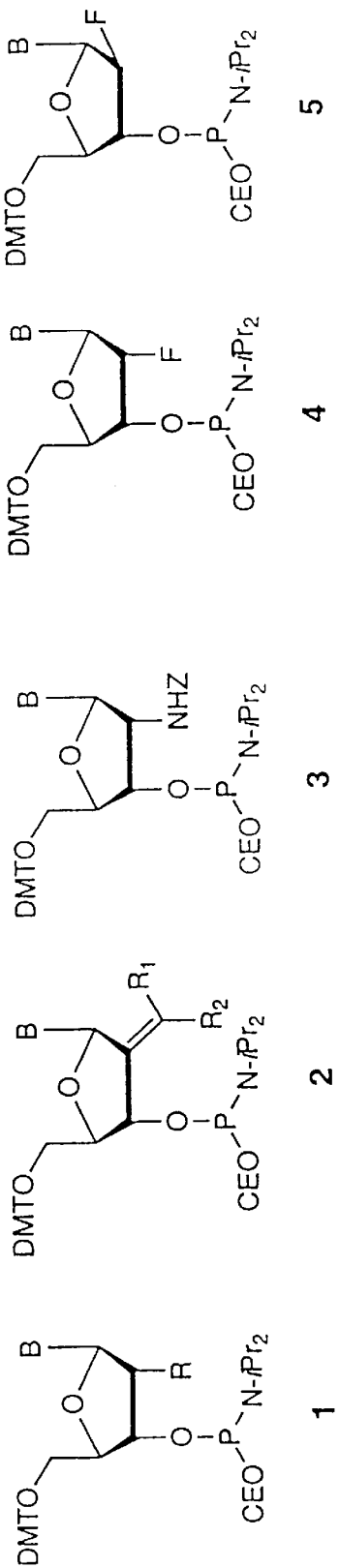
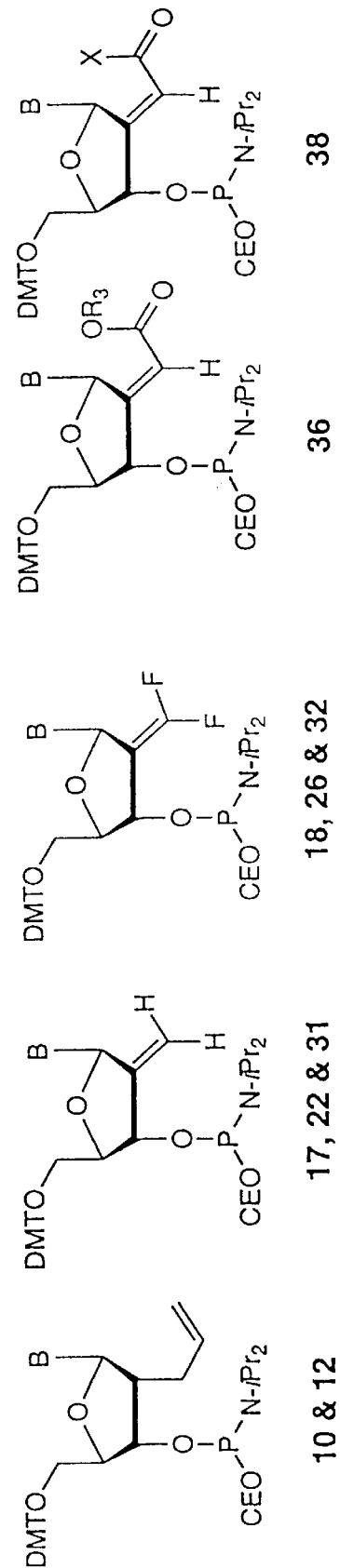
FIG. 6.
B = Protected A, C, G, U, T, 2AP, I, DiAP, P etc.

2'-DEOXY-2'-ALKYLNUCLEOTIDE CONTAINING NUCLEIC ACID

This is a continuation of application Ser. No. 08/218,934, filed Mar. 29, 1994, now U.S. Pat. No. 5,639,649, hereby incorporated by reference herein in totality, including drawings.

DESCRIPTION

Background of the Invention

This invention relates to chemically synthesized ribozymes, or enzymatic nucleic acid molecules, antisense oligonucleotides and derivatives thereof.

The following is a brief history of the discovery and activity of enzymatic RNA molecules or ribozymes. This history is not meant to be complete but is provided only for understanding of the invention that follows. This summary is not an admission that all of the work described below is prior art to the claimed invention.

Prior to the 1970s it was thought that all genes were direct linear representations of the proteins that they encoded. This simplistic view implied that all genes were like ticker tape messages, with each triplet of DNA "letters" representing one protein "word" in the translation. Protein synthesis occurred by first transcribing a gene from DNA into RNA (letter for letter) and then translating the RNA into protein (three letters at a time). In the mid 1970s it was discovered that some genes were not exact, linear representations of the proteins that they encode. These genes were found to contain interruptions in the coding sequence which were removed from, or "spliced out" of, the RNA before it became translated into protein. These interruptions in the coding sequence were given the name of intervening sequences (or introns) and the process of removing them from the RNA was termed splicing. After the discovery of introns, two questions immediately arose: i) why are introns present in genes in the first place, and ii) how do they get removed from the RNA prior to protein synthesis? The first question is still being debated, with no clear answer yet available. The second question, how introns get removed from the RNA, is much better understood after a decade and a half of intense research on this question. At least three different mechanisms have been discovered for removing introns from RNA. Two of these splicing mechanisms involve the binding of multiple protein factors which then act to correctly cut and join the RNA. A third mechanism involves cutting and joining of the RNA by the intron itself, in what was the first discovery of catalytic RNA molecules.

Cech and colleagues were trying to understand how RNA splicing was accomplished in a single-celled pond organism called *Tetrahymena thermophila*. They had chosen *Tetrahymena thermophila* as a matter of convenience, since each individual cell contains over 10,000 copies of one intron-containing gene (the gene for ribosomal RNA). They reasoned that such a large number of intron-containing RNA molecules would require a large amount of (protein) splicing factors to get the introns removed quickly. Their goal was to purify these hypothesized splicing factors and to demonstrate that the purified factors could splice the intron-containing RNA in vitro. Cech rapidly succeeded in getting RNA splicing to work in vitro, but something unusual was going on. As expected, splicing occurred when the intron-containing RNA was mixed with protein-containing extracts from Tetrahymena, but splicing also occurred when the protein extracts were left out. Cech proved that the intervening sequence RNA was acting as its own splicing factor to snip itself out of the surrounding RNA. They published this startling discovery in 1982. Continuing studies in the early 1980's served to elucidate the complicated structure of the Tetrahymena intron and to decipher the mechanism by which self-splicing occurs. Many research groups helped to demonstrate that the specific folding of the Tetrahymena intron is critical for bringing together the parts of the RNA that will be cut and spliced. Even after splicing is complete, the released intron maintains its catalytic structure. As a consequence, the released intron is capable of carrying out additional cleavage and splicing reactions on itself (to form intron circles). By 1986, Cech was able to show that a shortened form of the Tetrahymena intron could carry out a variety of cutting and joining reactions on other pieces of RNA. The demonstration proved that the Tetrahymena intron can act as a true enzyme: i) each intron molecule was able to cut many substrate molecules while the intron molecule remained unchanged, and ii) reactions were specific for RNA molecules that contained a unique sequence (CUCU) which allowed the intron to recognize and bind the RNA. Zaug and Cech coined the term "ribozyme" to describe any ribonucleic acid molecule that has enzyme-like properties. Also in 1986, Cech showed that the RNA substrate sequence recognized by the Tetrahymena ribozyme could be changed by altering a sequence within the ribozyme itself. This property has led to the development of a number of site-specific ribozymes that have been individually designed to cleave at other RNA sequences. The Tetrahymena intron is the most well-studied of what is now recognized as a large class of introns, Group I introns. The overall folded structure, including several sequence elements, is conserved among the Group I introns, as is the general mechanism of splicing. Like the Tetrahymena intron, some members of this class are catalytic, i.e. the intron itself is capable of the self-splicing reaction. Other Group I introns require additional (protein) factors, presumably to help the intron fold into and/or maintain its active structure. While the Tetrahymena intron is relatively large, (413 nucleotides) a shortened form of at least one other catalytic intron (SunY intron of phage T4, 180 nucleotides) may prove advantageous not only because of its smaller size but because it undergoes self-splicing at an even faster rate than the Tetrahymena intron.

Ribonuclease P (RNAseP) is an enzyme comprised of both RNA and protein components which are responsible for converting precursor tRNA molecules into their final form by trimming extra RNA off one of their ends. RNAseP activity has been found in all organisms tested, but the bacterial enzymes have been the most studied. The function of RNAseP has been studied since the mid-1970s by many labs. In the late 1970s, Sidney Altman and his colleagues showed that the RNA component of RNAseP is essential for its processing activity; however, they also showed that the protein component also was required for processing under their experimental conditions. After Cech's discovery of self-splicing by the Tetrahymena intron, the requirement for both protein and RNA components in RNAseP was reexamined. In 1983, Altman and Pace showed that the RNA was the enzymatic component of the RNAseP complex. This demonstrated that an RNA molecule was capable of acting as a true enzyme, processing numerous tRNA molecules without itself undergoing any change. The folded structure of RNAseP RNA has been determined, and while the sequence is not strictly conserved between RNAs from different organisms, this higher order structure is. It is thought that the protein component of the RNAseP complex may serve to stabilize the folded RNA in vivo. At least one RNA position important both to substrate recognition and to determination of the cleavage site has been identified, however little else is known about the active site. Because tRNA sequence recognition is minimal, it is clear that some aspect(s) of the tRNA structure must also be involved in substrate recognition and cleavage activity. The size of RNAseP RNA (>350 nucleotides), and the complexity of the substrate recognition, may limit the potential for the use of an RNAseP-like RNA in therapeutics. However, the size of RNAseP is being trimmed down (a molecule of only 290 nucleotides functions reasonably well). In addition, substrate recognition has been simplified by the recent discovery that RNAseP RNA can cleave small RNAs lacking the natural tRNA secondary structure if an additional RNA (containing a "guide" sequence and a sequence element naturally present at the end of all tRNAs) is present as well.

Symons and colleagues identified two examples of a self-cleaving RNA that differed from other forms of catalytic RNA already reported. Symons was studying the propagation of the avocado sunblotch viroid (ASV), an RNA virus that infects avocado plants. Symons demonstrated that as little as 55 nucleotides of the ASV RNA was capable of folding in such a way as to cut itself into two pieces. It is thought that in vivo self-cleavage of these RNAs is responsible for cutting the RNA into single genome-length pieces during viral propagation. Symons discovered that variations on the minimal catalytic sequence from ASV could be found in a number of other plant pathogenic RNAs as well. Comparison of these sequences revealed a common structural design consisting of three stems and loops connected by central loop containing many conserved (invariant from one RNA to the next) nucleotides. The predicted secondary structure for this catalytic RNA reminded the researchers of the head of a hammer consisting of three double helical domains, stems I, II and III and a catalytic core (FIGS. 1 and 2a); thus it was named as such. Uhlenbeck was successful in separating the catalytic region of the ribozyme from that of the substrate. Thus, it became possible to assemble a hammerhead ribozyme from 2 (or 3) small synthetic RNAs. A 19-nucleotide catalytic region and a 24-nucleotide substrate, representing division of the hammerhead domain along the axes of stems I and II (FIG. 2b) were sufficient to support specific cleavage. The catalytic domain of numerous hammerhead ribozymes have now been studied by both the Uhlenbeck and Symons groups with regard to defining the nucleotides required for specific assembly and catalytic activity and determining the rates of cleavage under various conditions.

Haseloff and Gerlach showed it was possible to divide the domains of the hammerhead ribozyme in a different manner, division of the hammerhead domain along the axes of stems I and III (FIG. 2c). By doing so, they placed most of the required sequences in the strand that didn't get cut (the ribozyme) and only a required UH where H=C, A, U in the strand that did get cut (the substrate). This resulted in a catalytic ribozyme that could be designed to cleave any UH RNA sequence embedded within a longer "substrate recognition" sequence. The specific cleavage of a long mRNA, in a predictable manner using several such hammerhead ribozymes, was reported in 1988. A further development was the division of the catalytic hammerhead domain along the axes of stems III and II (FIG. 2d, Jeffries and Symons, Nucleic Acids Res. 1989, 17, 1371–1377.)

One plant pathogen RNA (from the negative strand of the tobacco ringspot virus) undergoes self-cleavage but cannot be folded into the consensus hammerhead structure described above. Bruening and colleagues have independently identified a 50-nucleotide catalytic domain for this RNA. In 1990, Hampel and Tritz succeeded in dividing the catalytic domain into two parts that could act as substrate and ribozyme in a multiple-turnover, cutting reaction (FIG. 3). As with the hammerhead ribozyme, the hairpin catalytic portion contains most of the sequences required for catalytic activity while only a short sequence (GUC in this case) is required in the target. Hampel and Tritz described the folded structure of this RNA as consisting of a single hairpin and coined the term "hairpin" ribozyme (Bruening and colleagues use the term "paperclip" for this ribozyme motif, see, FIG. 3). Continuing experiments suggest an increasing number of similarities between the hairpin and hammerhead ribozymes in respect to both binding of target RNA and mechanism of cleavage. At the same time, the minimal size of the hairpin ribozyme is still 50–60% larger than the minimal hammerhead ribozyme.

Hepatitis Delta Virus (HDV) is a virus whose genome consists of single-stranded RNA. A small region (~80 nucleotides, FIG. 4) in both the genomic RNA, and in the complementary anti-genomic RNA, is sufficient to support self-cleavage. As the most recently discovered ribozyme, HDV's ability to self-cleave has only been studied for a few years, but is interesting because of its connection to a human disease. In 1991, Been and Perrotta proposed a secondary structure for the HDV RNAs that is conserved between the genomic and anti-genomic RNAs and is necessary for catalytic activity. Separation of the HDV RNA into "ribozyme" and "substrate" portions has recently been achieved by Been, but the rules for targeting different substrate RNAs have not yet been determined fully (see, FIG. 4). Been has also succeeded in reducing the size of the HDV ribozyme to ~60 nucleotides.

The table below lists some of the characteristics of the ribozymes discussed above:

TABLE 1

Characteristics of Ribozymes

Group I Introns

Size: ~300 to >1000 nucleotides.
Requires a U in the target sequence immediately 5' of the cleavage site.
Binds 4–6 nucleotides at 5' side of cleavage site.
Over 75 known members of this class. Found in *Tetrahymena thermaphila* rRNA, fungal mitochondria, chloroplasts, phage T4, blue-green algae, and others.
RNAseP RNA (M1 RNA)

Size: ~290 to 400 nucleotides.
RNA portion of a ribonucleoprotein enzyme. Cleaves tRNA precursors to form mature tRNA.
Roughly 10 known members of this group all are bacterial in origin.
Hammerhead Ribozyme Size: ~13 to 40 nucleotides.
Requires the target sequence UH immediately 5' of the cleavage site.
Binds a variable number nucleotides on both sides of the cleavage site.
14 known members of this class. Found in a number of plant pathogens (virusoids) that use RNA as the infectious agent (FIG. 1)
Hairpin Ribozyme Size: ~50 nucleotides.
Requires the target sequence GUC immediately 3' of the cleavage site.

TABLE 1-continued

Characteristics of Ribozymes

Binds 4 nucleotides at 5' side of the cleavage site and a variable number to the 3' side of the cleavage site.
Only 1 known member of this class. Found in one plant pathogen (satellite RNA of the tobacco ringspot virus) which uses RNA as the infectious agent (FIG. 3).

Hepatitis Delta Virus (HDV) Ribozyme

Size: ~60 nucleotides (at present).
Cleavage of target RNAs recently demonstrated.
Sequence requirements not fully determined.
Binding sites and structural requirements not fully determined, although no sequences 5' of cleavage site are required.
Only 1 known member of this class. Found in human HDV (FIG. 4).

Enzymatic nucleic acids act by first binding to a target RNA (or DNA, see Cech U.S. Pat. No. 5,180,818). Such binding occurs through the target binding portion of an enzymatic nucleic acid which is held in close proximity to an enzymatic portion of molecule that acts to cleave the target RNA. Thus, the enzymatic nucleic acid first recognizes and then binds a target RNA through complementary base-pairing, and once bound to the correct site, acts enzymatically to cut the target RNA. Cleavage of such a target RNA will destroy its ability to direct synthesis of an encoded protein. After an enzymatic nucleic acid has bound and cleaved its RNA target it is released from that RNA to search for another target and can repeatedly bind and cleave new targets. The enzymatic nature of a ribozyme is generally advantageous over other technologies, such as antisense technology (where a nucleic acid molecule simply binds to a nucleic acid target to block its translation) since the effective concentration of ribozyme necessary to effect a therapeutic treatment is lower than that of an antisense oligonucleotide. This advantage reflects the ability of the ribozyme to act enzymatically. Thus, a single ribozyme molecule is able to cleave many molecules of target RNA. In addition, the ribozyme is a highly specific inhibitor, with the specificity of inhibition depending not only on the base pairing mechanism of binding, but also on the mechanism by which the molecule inhibits the expression of the RNA to which it binds. That is, the inhibition is caused by cleavage of the RNA target and so specificity is defined as the ratio of the rate of cleavage of the targeted RNA over the rate of cleavage of non-targeted RNA. This cleavage mechanism is dependent upon factors additional to those involved in base pairing. Thus, it is thought that the specificity of action of a ribozyme is greater than that of antisense oligonucleotide binding the same RNA site.

By the phrase "enzymatic nucleic acid" is meant a catalytic modified-nucleotide containing nucleic acid molecule that has complementarity in a substrate binding region to a specified gene target, and also has an enzymatic activity that specifically cleaves RNA or DNA in that target. That is, the enzymatic nucleic acid is able to intramolecularly or intermolecularly cleave RNA or DNA and thereby inactivate a target RNA or DNA molecule. This complementarity functions to allow sufficient hybridization of the enzymatic RNA molecule to the target RNA or DNA to allow the cleavage to occur. 100% complementarity is preferred, but complementarity as low as 50–75% may also be useful in this invention.

In preferred embodiments of this invention, the enzymatic nucleic molecule is formed in a hammerhead motif, but may also be formed in the motif of a hairpin, hepatitis delta virus, group I intron or RNAseP RNA (in association with an RNA guide sequence). Examples of such hammerhead motifs are described by Rossi et al. *Aids Research and Human Retroviruses* 1992, 8, 183, of hairpin motifs by Hampel et al. "RNA Catalyst for Cleaving Specific RNA Sequences," filed Sep. 20, 1989, which is a continuation-in-part of U.S. Ser. No. 07/247,100 filed Sep. 20, 1988, Hampel and Tritz, *Biochemistry* 1989, 28, 4929 and Hampel et al. *Nucleic Acids Research* 1990, 18, 299, and an example of the hepatitis delta virus motif is described by Perrotta and Been, *Biochemistry* 1992, 31, 16, of the RNAseP motif by Guerrier-Takada et al. *Cell* 1983, 35, 849, and of the Group I intron by Cech et al. U.S. Pat. No. 4,987,071. These specific motifs are not limiting in the invention and those skilled in the art will recognize that all that is important in an enzymatic nucleic acid molecule of this invention is that it has a specific substrate binding site which is complementary to one or more of the target gene RNA or DNA regions, and that it have nucleotide sequences within or surrounding that substrate binding site which impart an RNA or DNA cleaving activity to the molecule.

The invention provides a method for producing a class of enzymatic cleaving agents or antisense molecules which exhibit a high degree of specificity for the RNA or DNA of a desired target. The enzymatic nucleic acid or antisense molecule is preferably targeted to a highly conserved sequence region of a target such that specific treatment of a disease or condition can be provided with a single enzymatic nucleic acid. Such nucleic acid molecules can be delivered exogenously to specific cells as required. In the preferred hammerhead motif the small size (less than 60 nucleotides, preferably between 30–40 nucleotides in length) of the molecule allows the cost of treatment to be reduced compared to other ribozyme motifs.

Synthesis of nucleic acids greater than 100 nucleotides in length is difficult using automated methods, and the therapeutic cost of such molecules is prohibitive. In this invention, small enzymatic nucleic acid motifs (e.g., of the hammerhead structure) are used for exogenous delivery. The simple structure of these molecules increases the ability of the enzymatic nucleic acid to invade targeted regions of the mRNA structure. Unlike the situation when the hammerhead structure is included within longer transcripts, there are no non-enzymatic nucleic acid flanking sequences to interfere with correct folding of the enzymatic nucleic acid structure or with complementary regions.

Eckstein et al. International Publication No. WO 92/07065, Perrault et al. *Nature* 1990, 344, 565–568, Pieken et al. *Science* 1991, 253, 314–317, Usman, N.; Cedergren, R. J. *Trends in Biochem. Sci.* 1992, 17, 334–339, Usman et al. U.S. patent application Ser. No. 07/829,729, and Sproat, B. European Patent Application 92110298.4 describe various chemical modifications that can be made to the sugar moieties of enzymatic RNA molecules. Usman et al. also describe various required ribonucleotides in a ribozyme, and methods by which such nucleotides can be defined. De Mesmaeker et al. *Syn. Lett.* 1993, 677–680 (not admitted to be prior art to the present invention) describes the synthesis of certain 2'-C-alkyl uridine and thymidine derivatives. They conclude that ". . . their use in an antisense approach seems to be very limited."

SUMMARY OF THE INVENTION

This invention relates to the use of 2'-deoxy-2'-alkylnucleotides in oligonucleotides, which are particularly useful for enzymatic cleavage of RNA or single-stranded DNA, and also as antisense oligonucleotides. As the term is used in this application, 2'-deoxy-2'-alkylnucleotide-containing enzymatic nucleic acids are catalytic nucleic molecules that contain 2'-deoxy-2'-alkylnucleotide components replacing, but not limited to, double stranded stems, single stranded "catalytic core" sequences, single-stranded loops or single-stranded recognition sequences. These molecules are able to cleave (preferably, repeatedly cleave) separate RNA or DNA molecules in a nucleotide base sequence specific manner. Such catalytic nucleic acids can also act to cleave intramolecularly if that is desired. Such enzymatic molecules can be targeted to virtually any RNA transcript.

Also within the invention are 2'-deoxy-2'-alkylnucleotides which may be present in enzymatic nucleic acid or even in antisense oligonucleotides. Contrary to the findings of De Mesmaeker et al. applicant has found that such nucleotides are useful since they enhance the stability of the antisense or enzymatic molecule, and can be used in locations which do not affect the desired activity of the molecule. That is, while the presence of the 2'-alkyl group may reduce binding affinity of the oligonucleotide containing this modification, if that moiety is not in an essential base pair forming region then the enhanced stability that it provides to the molecule is advantageous. In addition, while the reduced binding may reduce enzymatic activity, the enhanced stability may make the loss of activity of less consequence. Thus, for example, if a 2'-deoxy-2'-alkyl-containing molecule has 10% the activity of the unmodified molecule, but has 10-fold higher stability in vivo then it has utility in the present invention. The same analysis is true for antisense oligonucleotides containing such modifications. The invention also relates to novel intermediates useful in the synthesis of such nucleotides and oligonucleotides (examples of which are shown in the Figures), and to methods for their synthesis.

Thus, in a first aspect, the invention features 2'-deoxy-2'-alkylnucleotides, that is a nucleotide base having at the 2'-position on the sugar molecule an alkyl moiety and in preferred embodiments features those where the nucleotide is not uridine or thymidine. That is, the invention preferably includes all those nucleotides useful for making enzymatic nucleic acids or antisense molecules that are not described by the art discussed above.

Examples of various alkyl groups useful in this invention are shown in FIG. 6, where each R group is any alkyl. These examples are not limiting in the invention. Specifically, an "alkyl" group refers to a saturated aliphatic hydrocarbon, including straight-chain, branched-chain, and cyclic alkyl groups. Preferably, the alkyl group has 1 to 12 carbons. More preferably it is a lower alkyl of from 1 to 7 carbons, more preferably 1 to 4 carbons. The alkyl group may be substituted or unsubstituted. When substituted the substituted group(s) is preferably, hydroxyl, cyano, alkoxy, $=O$, $=S$, $NO_2$ or $N(CH_3)_2$, amino, or SH. The term also includes alkenyl groups which are unsaturated hydrocarbon groups containing at least one carbon—carbon double bond, including straight-chain, branched-chain, and cyclic groups. Preferably, the alkenyl group has 1 to 12 carbons. More preferably it is a lower alkenyl of from 1 to 7 carbons, more preferably 1 to 4 carbons. The alkenyl group may be substituted or unsubstituted. When substituted the substituted group(s) is preferably, hydroxyl, cyano, alkoxy, $=O$, $=S$, $NO_2$, halogen, $N(CH_3)_2$, amino, or SH. The term "alkyl" also includes alkynyl groups which have an unsaturated hydrocarbon group containing at least one carbon—carbon triple bond, including straight-chain, branched-chain, and cyclic groups. Preferably, the alkynyl group has 1 to 12 carbons. More preferably it is a lower alkynyl of from 1 to 7 carbons, more preferably 1 to 4 carbons. The alkynyl group may be substituted or unsubstituted. When substituted the substituted group(s) is preferably, hydroxyl, cyano, alkoxy, $=O$, $=S$, $NO_2$ or $N(CH_3)_2$, amino or SH. The term "alkyl" does not include alkoxy groups which have an "—O—alkyl" group, where "alkyl" is defined as described above, where the O is adjacent the 2'-position of the sugar molecule.

Such alkyl groups may also include aryl, alkylaryl, carbocyclic aryl, heterocyclic aryl, amide and ester groups. An "aryl" group refers to an aromatic group which has at least one ring having a conjugated pi electron system and includes carbocyclic aryl, heterocyclic aryl and biaryl groups, all of which may be optionally substituted. The preferred substituent(s) of aryl groups are halogen, trihalomethyl, hydroxyl, SH, OH, cyano, alkoxy, alkyl, alkenyl, alkynyl, and amino groups. An "alkylaryl" group refers to an alkyl group (as described above) covalently joined to an aryl group (as described above. Carbocyclic aryl groups are groups wherein the ring atoms on the aromatic ring are all carbon atoms. The carbon atoms are optionally substituted. Heterocyclic aryl groups are groups having from 1 to 3 heteroatoms as ring atoms in the aromatic ring and the remainder of the ring atoms are carbon atoms. Suitable heteroatoms include oxygen, sulfur, and nitrogen, and include furanyl, thienyl, pyridyl, pyrrolyl, N-lower alkyl pyrrolo, pyrimidyl, pyrazinyl, imidazolyl and the like, all optionally substituted. An "amide" refers to an —C(O)—NH—R, where R is either alkyl, aryl, alkylaryl or hydrogen. An "ester" refers to an —C(O)—OR', where R is either alkyl, aryl, alkylaryl or hydrogen.

In other aspects, also related to those discussed above, the invention features oligonucleotides having one or more 2'-deoxy-2'-alkylnucleotides (preferably not a 2'-alkyl- uridine or thymidine); e.g. enzymatic nucleic acids having a 2'-deoxy-2'-alkylnucleotide; and a method for producing an enzymatic nucleic acid molecule having enhanced activity to cleave an RNA or single-stranded DNA molecule, by forming the enzymatic molecule with at least one nucleotide having at its 2'-position an alkyl group. In other related aspects, the invention features 2'-deoxy-2'-alkylnucleotide triphosphates. These triphosphates can be used in standard protocols to form useful oligonucleotides of this invention.

The 2'-alkyl derivatives of this invention provide enhanced stability to the oligonulceotides containing them. While they may also reduce absolute activity in an in vitro assay they will provide enhanced overall activity in vivo. Below are provided assays to determine which such molecules are useful. Those in the art will recognize that equivalent assays can be readily devised.

In another aspect, the invention features hammerhead motifs having enzymatic activity having ribonucleotides at locations shown in FIG. 5 at 5, 6, 8, 12, and 15.1, and having substituted ribonucleotides at other positions in the core and in the substrate binding arms if desired. (The term "core" refers to positions between bases 3 and 14 in FIG. 5, and the binding arms correspond to the bases from the 3'-end to base 15.1, and from the 5'-end to base 2). Applicant has found that use of ribonucleotides at these five locations in the core provide a molecule having sufficient enzymatic activity even when modified nucleotides are present at other sites in the motif. Other such combinations of useful ribonucleotides can be determined as described by Usman et al. supra.

Other features and advantages of the invention will be apparent from the following description of the preferred embodiments thereof, and from the claims.

DESCRIPTION OF THE PREFERRED EMBODIMENTS

The drawings will first briefly be described.

BRIEF DESCRIPTION OF THE DRAWINGS

FIG. 1 is a diagrammatic representation of the hammerhead ribozyme domain known in the art, numbered according to Hertel et al. *Nucleic Acids Res.* 1992, 20, 3252.

FIG. 6 shows the structures of various 2'-alkyl modified nucleotides which exemplify those of this invention. R groups are alkyl groups, Z is a protecting group.

Figure 1:
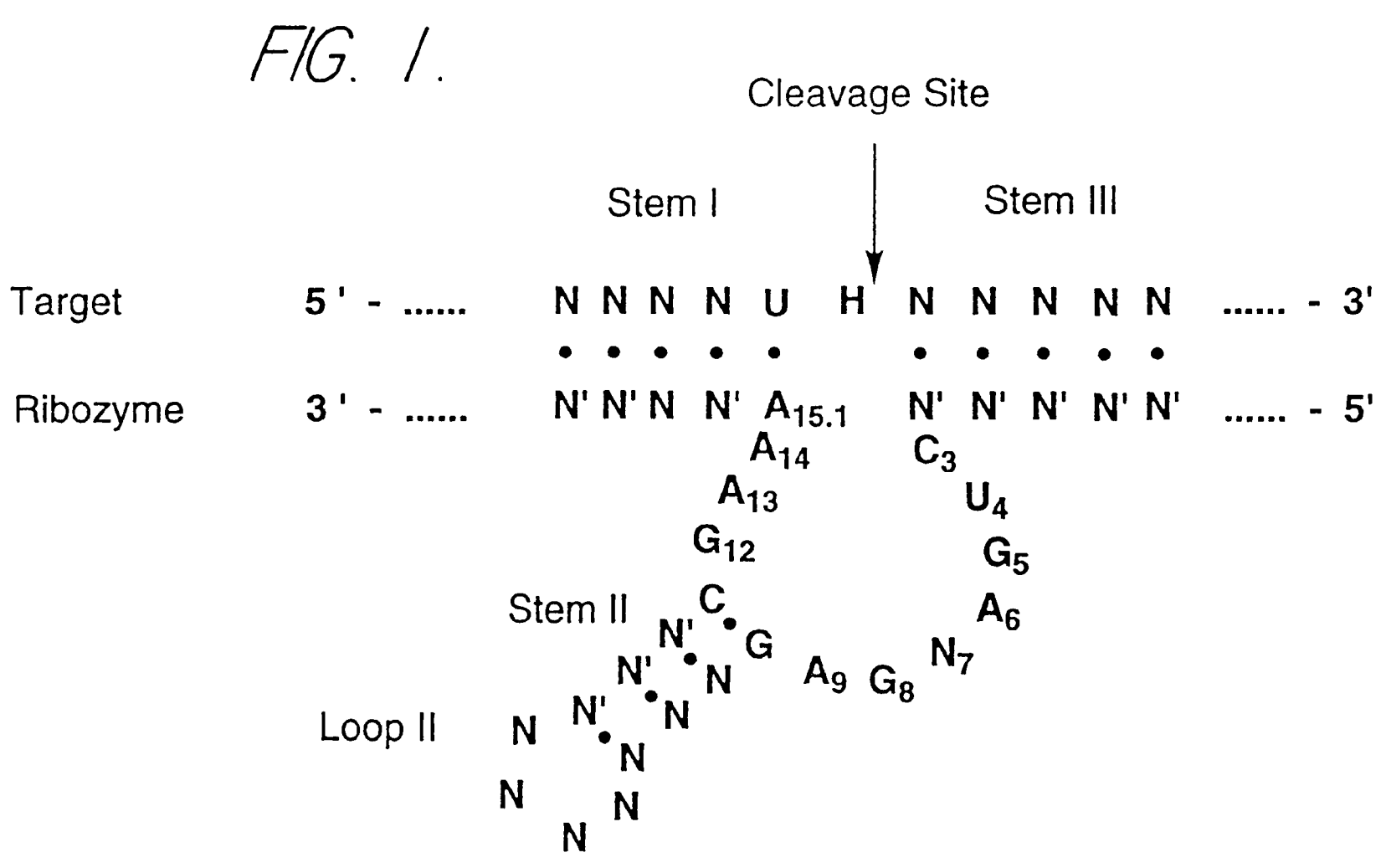

Table 2 is a summary of specified catalytic parameters ($t_A$ and $t_S$) on short substrates in vitro, and stabilities of the noted modified catalytic nucleic acids in human serum. U4 and U7 refer to the uracil bases noted in FIG. 1. Modifications at the 2'-position are shown in the table.

TABLE 2

| Entry | Modification | t½ (m) Activity ($t_A$) | t½ (m) Stability ($t_S$) | $\beta = t_S/t_A \times 10$ |
|---|---|---|---|---|
| 1 | U4 & U7 = U | 1 | 0.1 | 1 |
| 2 | U4 & U7 = 2'-O-Me-U | 4 | 260 | 650 |
| 3 | U4 = 2' = $CH_2$-U | 6.5 | 120 | 180 |
| 4 | U7 = 2' = $CH_2$-U | 8 | 280 | 350 |
| 5 | U4 & U7 = 2' = $CH_2$-U | 9.5 | 120 | 130 |
| 6 | U4 = 2' = $CF_2$-U | 5 | 320 | 640 |
| 7 | U7 = 2' = $CF_2$-U | 4 | 220 | 550 |
| 8 | U4 & U7 = 2' = $CF_2$-U | 20 | 320 | 160 |
| 9 | U4 = 2'-F-U | 4 | 320 | 800 |
| 10 | U7 = 2'-F-U | 8 | 400 | 500 |

TABLE 2-continued

| Entry | Modification | t½ (m) Activity ($t_A$) | t½ (m) Stability ($t_S$) | $\beta = t_S/t_A \times 10$ |
|---|---|---|---|---|
| 11 | U4 & U7 = 2'-F-U | 4 | 300 | 750 |
| 12 | U4 = 2'-C-Allyl-U | 3 | >500 | >1700 |
| 13 | U7 = 2'-C-Allyl-U | 3 | 220 | 730 |
| 14 | U4 & U7 = 2'-C-Allyl-U | 3 | 120 | 400 |
| 15 | U4 = 2'-araF-U | 5 | >500 | >1000 |
| 16 | U7 = 2'-araF-U | 4 | 350 | 875 |
| 17 | U4 & U7= 2'-araF-U | 15 | 500 | 330 |
| 18 | U4 = 2'-$NH_2$-U | 10 | 500 | 500 |
| 19 | U7 = 2'-$NH_2$-U | 5 | 500 | 1000 |
| 20 | U4 & U7 = 2'-$NH_2$-U | 2 | 300 | 1500 |
| 21 | U4 = dU | 6 | 100 | 170 |
| 22 | U4 & U7 = dU | 4 | 240 | 600 |

Figure 2:
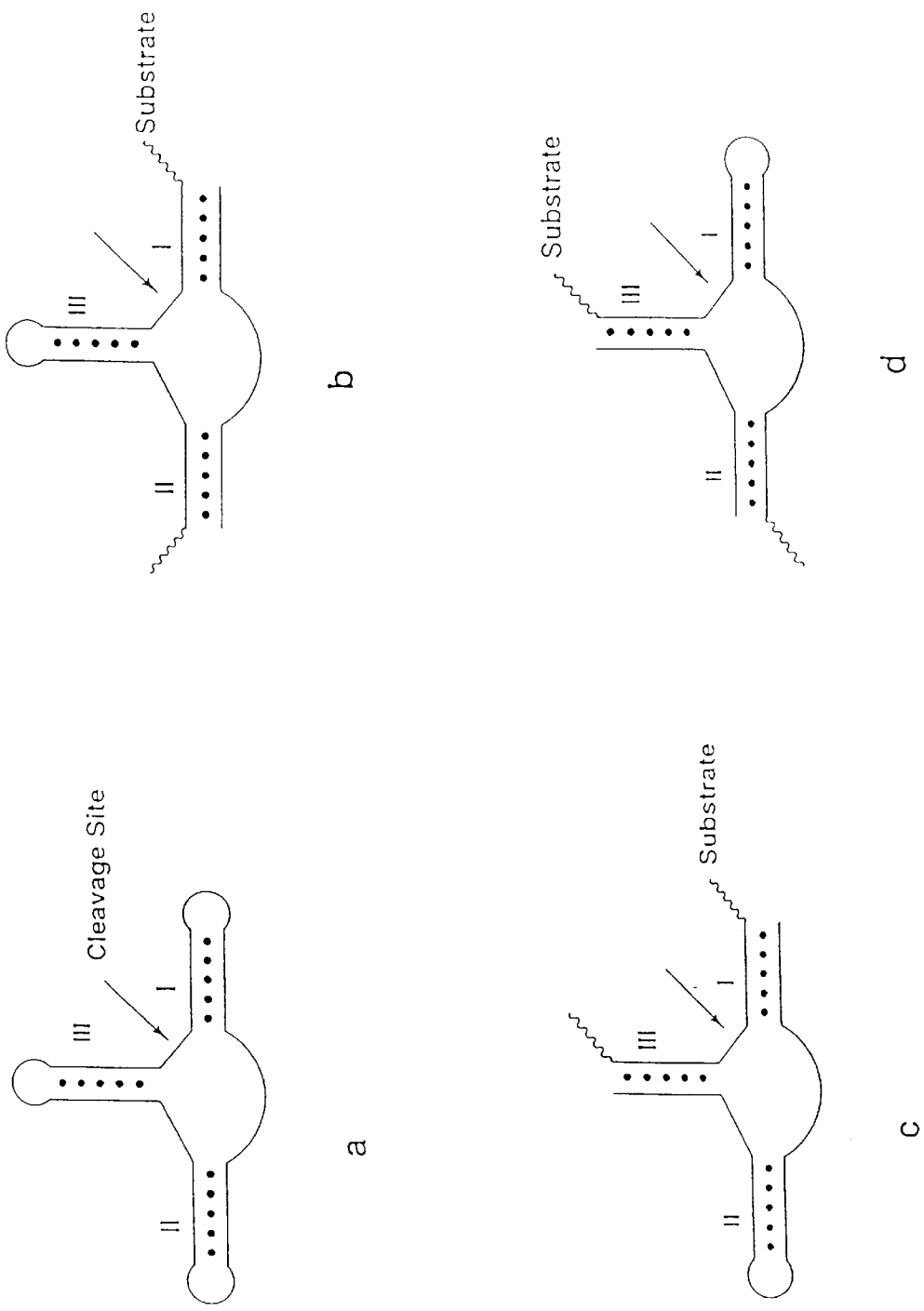
FIG. 2a is a diagrammatic representation of the hammerhead ribozyme domain known in the art.
FIG. 2b is a diagrammatic representation of the hammerhead ribozyme as divided by Uhlenbeck (*Nature* 1987, 327, 596–600) into a substrate and enzyme portion.
FIG. 2c is a similar diagram showing the hammerhead divided by Haseloff and Gerlach (*Nature* 1988, 334, 585–591) into two portions.
FIG. 2d is a similar diagram showing the hammerhead divided by Jeffries and Symons (*Nucleic Acids Res.* 1989, 17, 1371–1371) into two portions.
Figure 3:
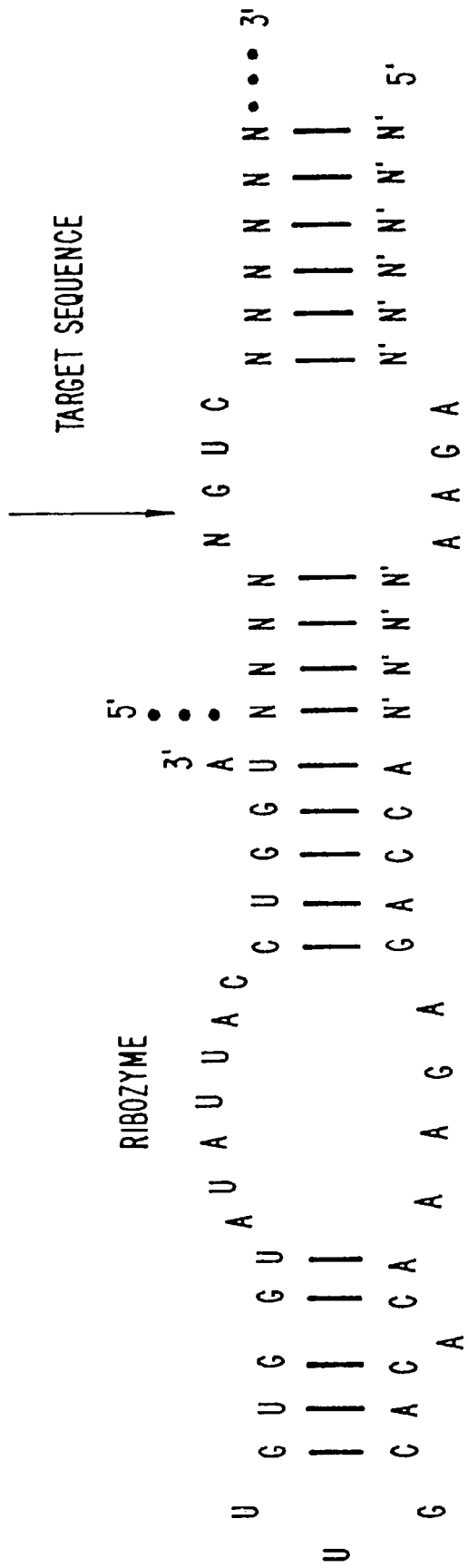
FIG. 3 is a representation of general the structure of the hairpin ribozyme domain known in the art.
Figure 4:
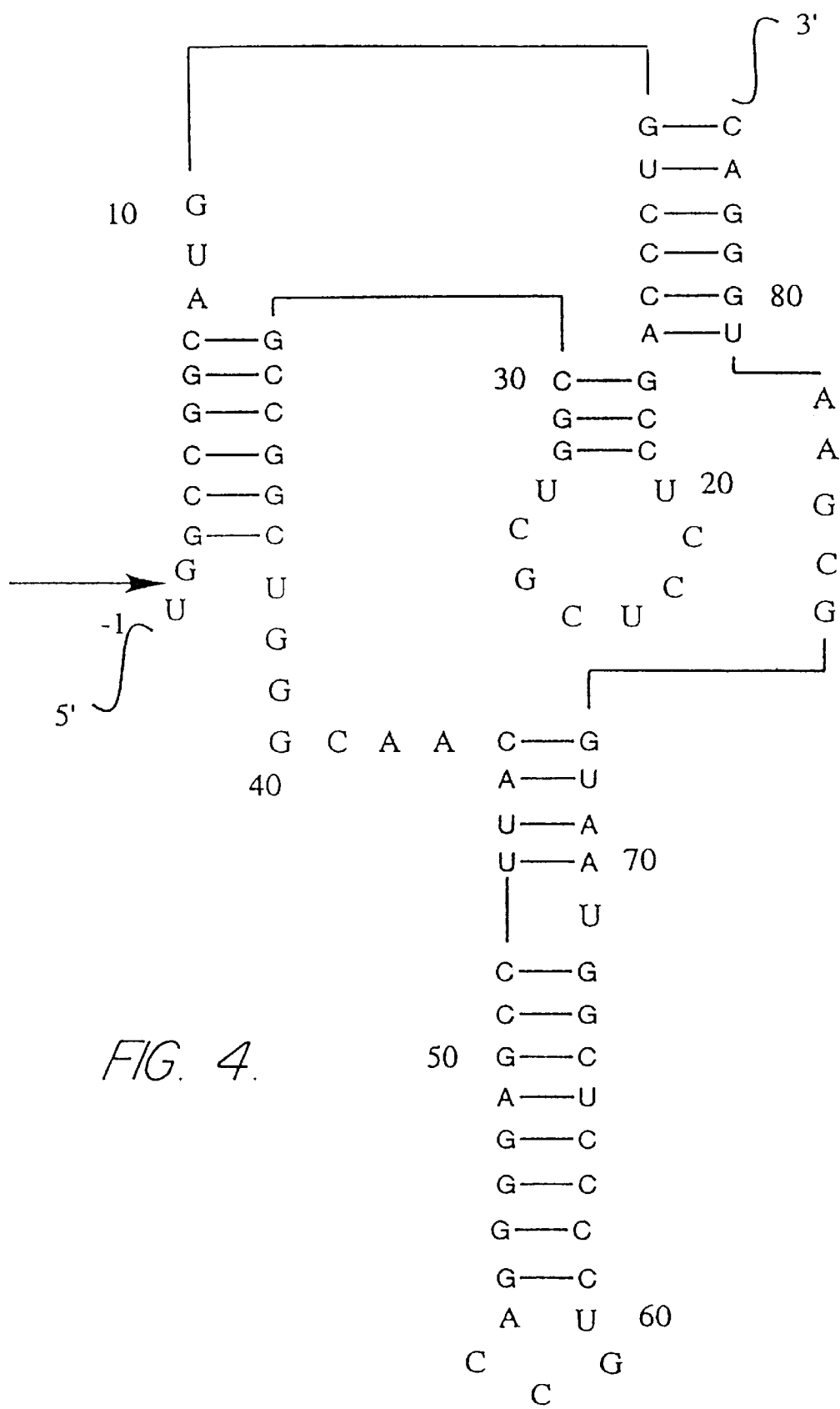
FIG. 4 is a representation of the general structure of the hepatitis delta virus ribozyme domain known in the art.
Figure 5:
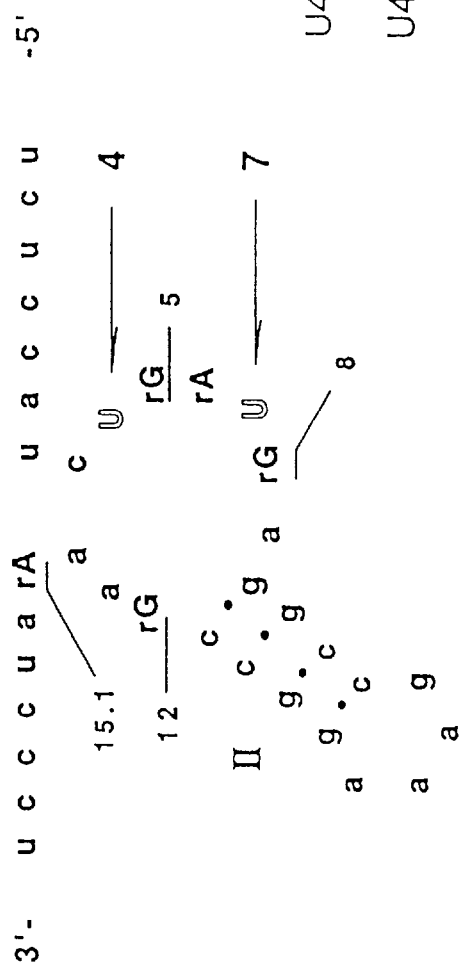
FIG. 5 is a diagrammatic representation of a position numbered hammerhead ribozyme (according to Hertel et al. *Nucleic Acids Res.* 1992, 20, 3252) showing specific substitutions.
Figure 7:
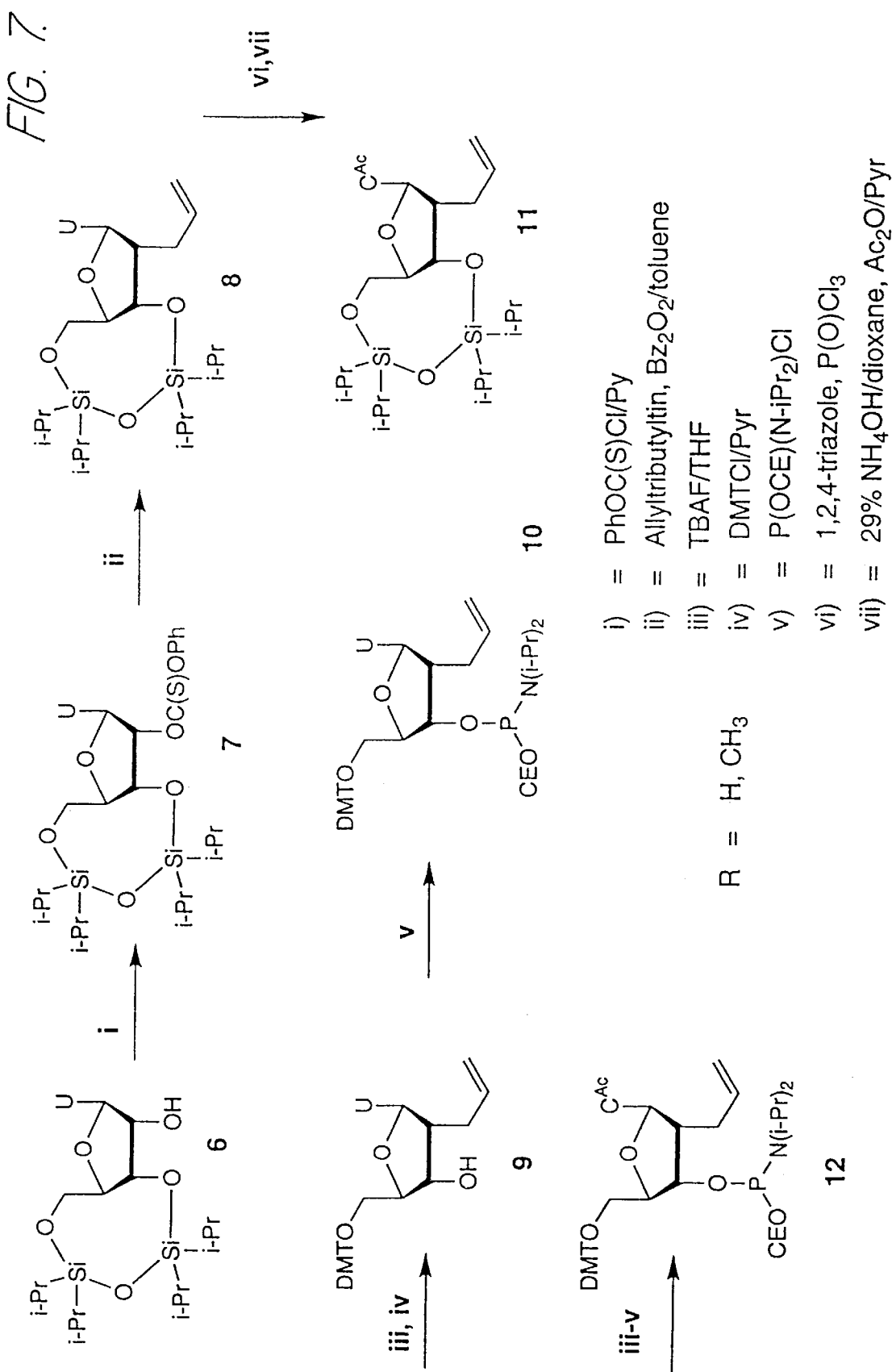
FIG. 7 is a diagrammatic representation of the synthesis of 2'-C-allyl uridine and cytidine.
Figure 8:
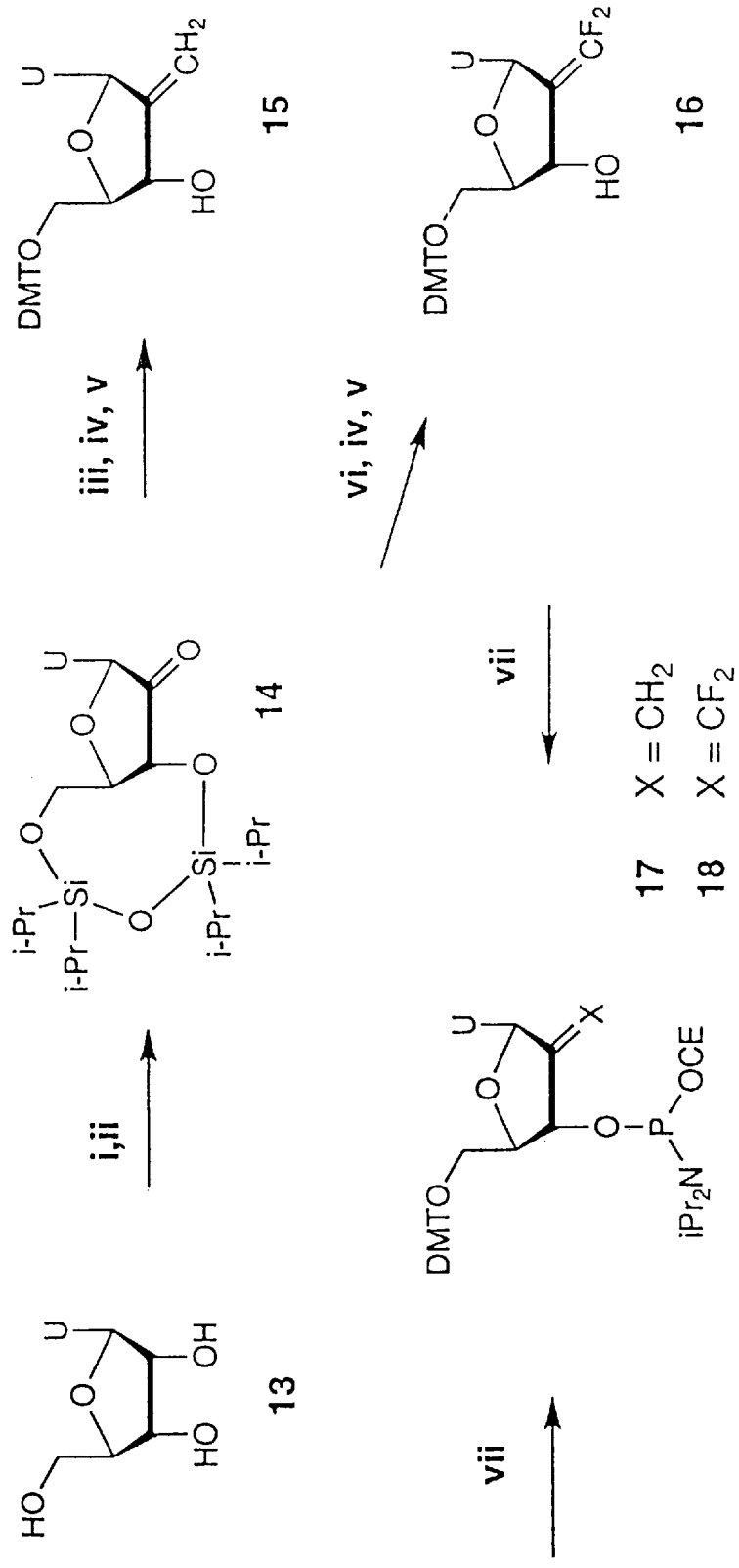
FIG. 8 is a diagrammatic representation of the synthesis of 2'-C-methylene and 2'-difluoromethylene uridine.
Figure 9:
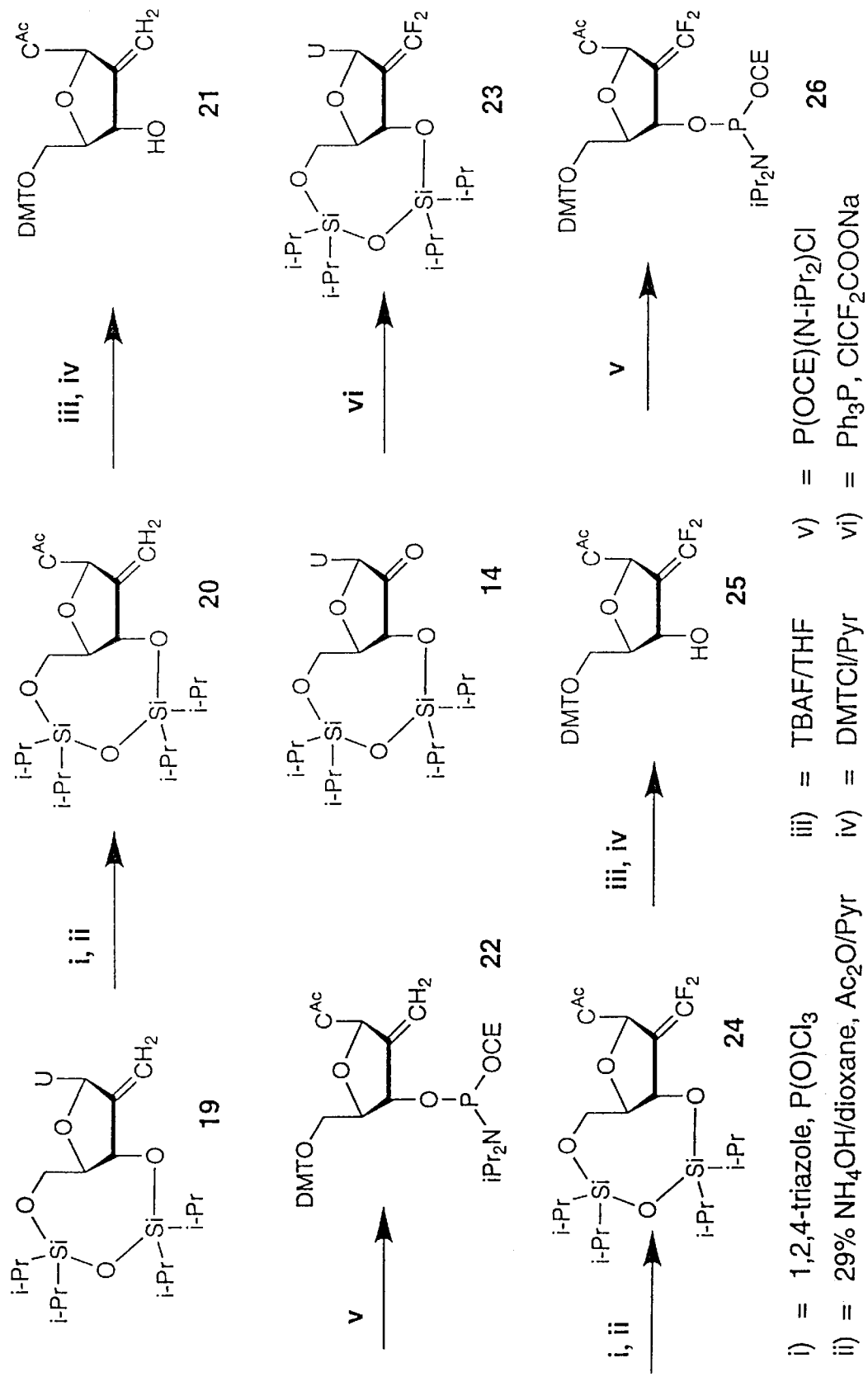
FIG. 9 is a diagrammatic representation of the synthesis of 2'-C-methylene and 2'-C-difluoromethylene cytidine.
Figure 10:
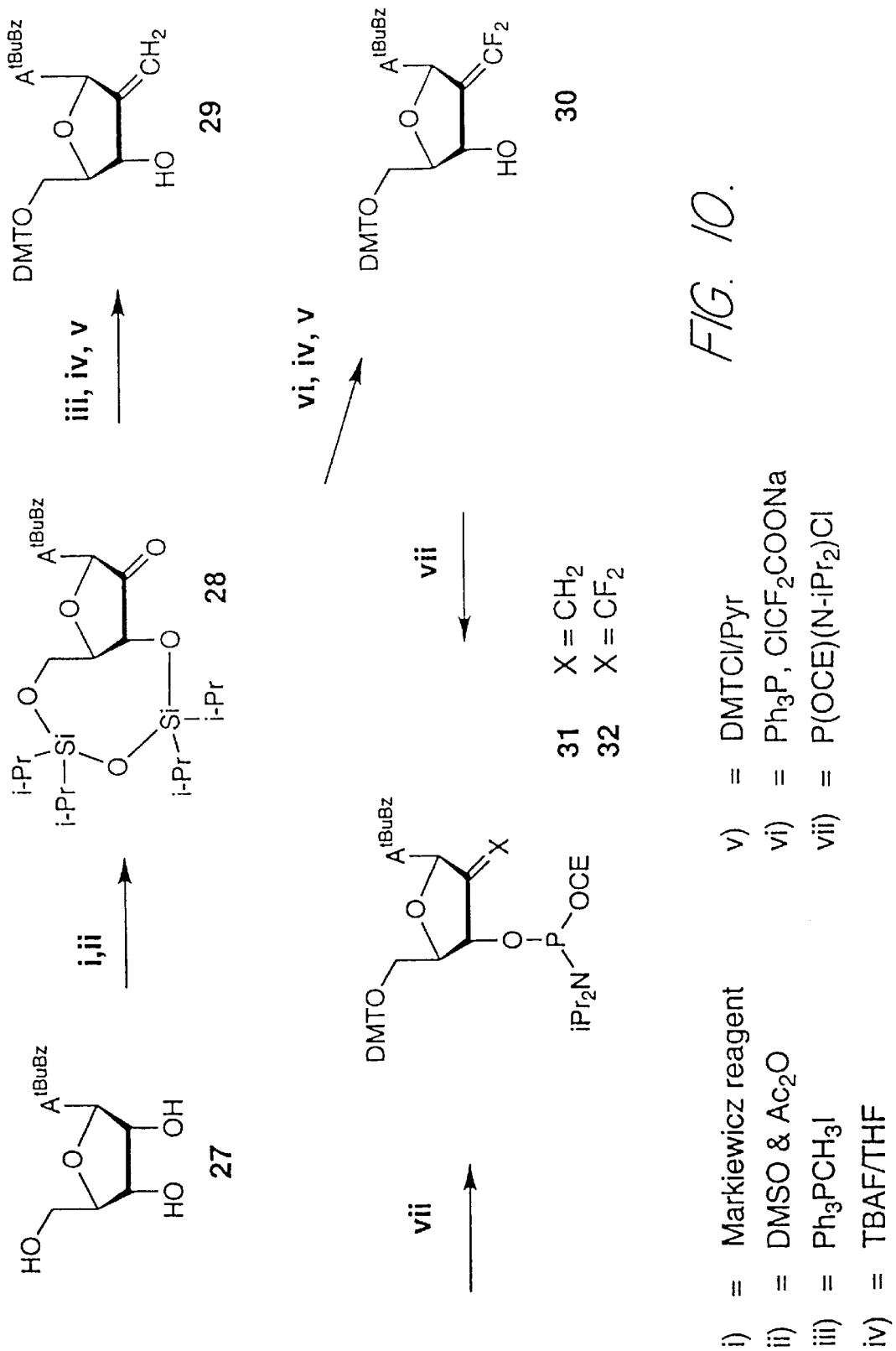
FIG. 10 is a diagrammatic representation of the synthesis of 2'-C-methylene and 2'-C-difluoromethylene adenosine.

FIG. 5 shows base numbering of a hammerhead motif in which the numbering of various nucleotides in a hammerhead ribozyme is provided. This is not to be taken as an indication that the Figure is prior art to the pending claims, or that the art discussed is prior art to those claims. Referring to FIG. 5, the preferred sequence of a hammerhead ribozyme in a 5'- to 3'-direction of the catalytic core is CUGANGAG [base paired with]CGAAA. In this invention, the use of 2'-C-alkyl substituted nucleotides that maintain or enhance the catalytic activity and or nuclease resistance of the hammerhead ribozyme is described. Although substitutions of any nucleotide with any of the modified nucleotides shown in FIG. 6 are possible, and were indeed synthesized, the basic structure composed of primarily 2'-O-Me nucleotides with selected substitutions was chosen to maintain maximal catalytic activity (Yang et al. *Biochemistry* 1992, 31, 5005–5009 and Paolella et al. *EMBO J.* 1992, 11, 1913–1919) and ease of synthesis, but is not limiting to this invention.

Ribozymes from FIG. 5 and Table 2 were synthesized and assayed for catalytic activity and nuclease resistance. With the exception of entries 8 and 17, all of the modified ribozymes retained at least ¹⁄₁₀ of the wild-type catalytic activity. From Table 2, all 2'-modified ribozymes showed very large and significant increases in stability in human serum (shown) and in the other fluids described below (Example 3, data not shown). The order of most aggressive nuclease activity was fetal bovine serum>human serum>human plasma>human synovial fluid. As an overall measure of the effect of these 2'-substitutions on stability and activity, a ratio $\beta$ was calculated (Table 2). This $\beta$ value indicated that all modified ribozymes tested had significant, >100–>1700 fold, increases in overall stability and activity. These increases in $\beta$ indicate that the lifetime of these modified ribozymes in vivo are significantly increased which should lead to a more pronounced biological effect.

More general substitutions of the 2'-modified nucleotides from FIG. 6 also increased the $t_{1/2}$ of the resulting modified ribozymes. However the catalytic activity of these ribozymes was decreased>10-fold.

Figure 11:
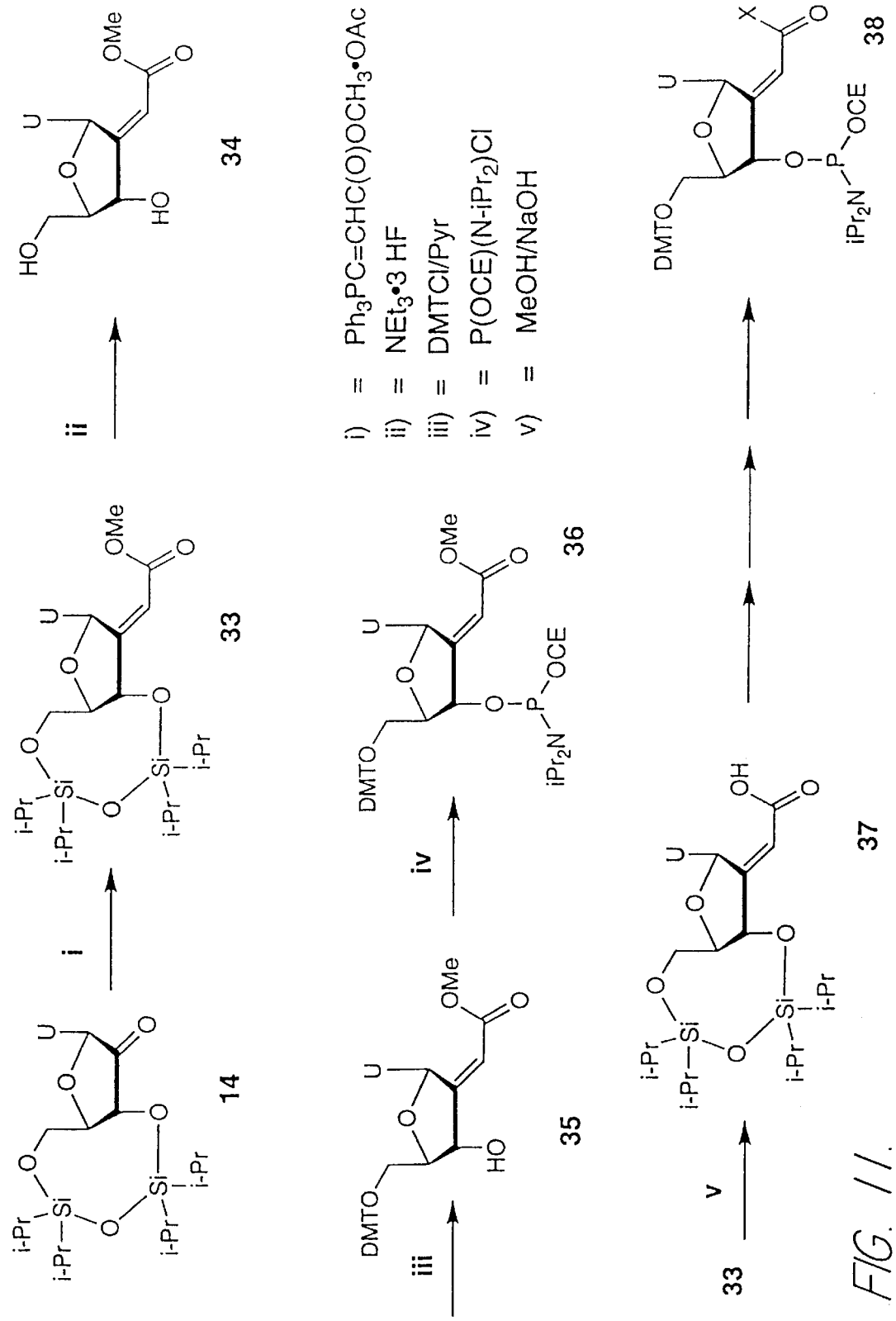
FIG. 11 is a diagrammatic representation of the synthesis of 2'-C-carboxymethylidine uridine, 2'-C-methoxycarboxymethylidine uridine and derivatized amidites thereof. X is $CH_3$ or alkyl as discussed above, or another substituent.

In FIG. 11 compound 37 may be used as a general intermediate to prepare derivatized 2'-C-alkyl phosphoramidites, where X is $CH_3$, or an alkyl, or other group described above.

EXAMPLES

The following are non-limiting examples showing the synthesis of nucleic acids using 2'-C-alkyl substituted phosphoramidites, the syntheses of the amidites, their testing for enzymatic activity and nuclease resistance.

Example 1

Synthesis of Hammerhead Ribozymes Containing 2'-Deoxy-2'-Alkylnucleotides & Other 2'-Modified Nucleotides The method of synthesis used generally follows the procedure for normal RNA synthesis as described in Usman, N.; Ogilvie, K. K.; Jiang, M. -Y.; Cedergren, R. J. *J. Am. Chem. Soc.* 1987, 109, 7845–7854 and in Scaringe, S. A.; Franklyn, C.; Usman, N. *Nucleic Acids Res.* 1990, 18, 5433–5441 and makes use of common nucleic acid protecting and coupling groups, such as dimethoxytrityl at the 5'-end, and phosphoramidites at the 3'-end (compounds 10, 12, 17, 22, 31, 18, 26, 32, 36 and 38). Other 2'-modified phosphoramidites were prepared according to: 3 & 4, Eckstein et al. International Publication No. WO 92/07065; and 5 Kois et al. *Nucleosides & Nucleotides* 1993, 12, 1093–1109. The average stepwise coupling yields were ~98%. The 2'-substituted phosphoramidites were incorporated into hammerhead ribozymes as shown in FIG. 5. However, these 2'-alkyl substituted phosphoramidites may be incorporated not only into hammerhead ribozymes, but also into hairpin, hepatitis delta virus, Group 1 or Group 2 intron catalytic nucleic acids, or into antisense oligonucleotides. They are, therefore, of general use in any nucleic acid structure.

Example 2

Ribozyme Activity Assay

Purified 5'-end labeled RNA substrates (15–25-mers) and purified 5'-end labeled ribozymes (~36-mers) were both heated to 95° C., quenched on ice and equilibrated at 37° C., separately. Ribozyme stock solutions were 1 mM, 200 nM, 40 nM or 8 nM and the final substrate RNA concentrations were ~1 nM. Total reaction volumes were 50 mL. The assay buffer was 50 mM Tris-Cl, pH 7.5 and 10 mM $MgCl_2$. Reactions were initiated by mixing substrate and ribozyme solutions at t=0. Aliquots of 5 mL were removed at time points of 1, 5, 15, 30, 60 and 120 m. Each time point was quenched in formamide loading buffer and loaded onto a 15% denaturing polyacrylamide gel for analysis. Quantitative analyses were performed using a phosphorimager (Molecular Dynamics).

Example 3

Stability Assay 500 pmol of gel-purified 5'-end-labeled ribozymes were precipitated in ethanol and pelleted by centrifugation. Each pellet was resuspended in 20 mL of appropriate fluid (human serum, human plasma, human synovial fluid or fetal bovine serum) by vortexing for 20 s at room temperature. The samples were placed into a 37° C. incubator and 2 mL aliquots were withdrawn after incubation for 0, 15, 30, 45, 60, 120, 240 and 480 m. Aliquots were added to 20 mL of a solution containing 95% formamide and 0.5X TBE (50 mM Tris, 50 mM borate, 1 mM EDTA) to quench further nuclease activity and the samples were frozen until loading onto gels. Ribozymes were size-fractionated by electrophoresis in 20% acrylamide/8M urea gels. The amount of intact ribozyme at each time point was quantified by scanning the bands with a phosphorimager (Molecular Dynamics) and the half-life of each ribozyme in the fluids was determined by plotting the percent intact ribozyme vs the time of incubation and extrapolation from the graph.

Example 4

3',5'-O-(Tetraisopropyl-disiloxane-1,3-diyl)-2'-O-Phenoxythiocarbonyl-Uridine (7)

To a stirred solution of 3',5'-O-(tetraisopropyl-disiloxane-1,3-diyl)-uridine, 6, (15.1 g, 31 mmol, synthesized according to *Nucleic Acid Chemistry*, ed. Leroy Townsend, 1986 pp. 229–231) and dimethylamino-pyridine (7.57 g, 62 mmol) a solution of phenylchlorothionoformate (5.15 mL, 37.2 mmol) in 50 mL of acetonitrile was added dropwise and the reaction stirred for 8 h. TLC (EtOAc:hexanes/1:1) showed disappearance of the starting material. The reaction mixture was evaporated, the residue dissolved in chloroform, washed with water and brine, the organic layer was dried over sodium sulfate, filtered and evaporated to dryness. The residue was purified by flash chromatography on silica gel with EtOAc:hexanes/2:1 as eluent to give 16.44 g (85%) of 7.

Example 5

3',5'-O-(Tetraisopropyl-disiloxane-1,3-diyl)-2'-C-Allyl -Uridine (8)

To a refluxing, under argon, solution of 3',5'-O-(tetraisopropyl-disiloxane-1,3-diyl)-2'-O-phenoxythiocarbonyl-uridine, 7, (5 g, 8.03 mmol) and allyl-tributyltin (12.3 mL, 40.15 mmol) in dry toluene, benzoyl peroxide (0.5 g) was added portionwise during 1 h. The resulting mixture was allowed to reflux under argon for an additional 7–8 h. The reaction was then evaporated and the product 8 purified by flash chromatography on silica gel with EtOAc:hexanes/1:3 as eluent. Yield 2.82 g (68.7%).

Example 6

5'-O-Dimethoxytrityl-2'-C-Allyl-Uridine (9)

A solution of 8 (1.25 g, 2.45 mmol) in 10 mL of dry tetrahydrofuran (THF) was treated with a 1 M solution of tetrabutylammoniumfluoride in THF (3.7 mL) for 10 m at room temperature. The resulting mixture was evaporated, the residue was loaded onto a silica gel column, washed with 1 L of chloroform, and the desired deprotected compound was eluted with chloroform:methanol/9:1. Appropriate fractions were combined, solvents removed by evaporation, and the residue was dried by coevaporation with dry pyridine. The oily residue was redissolved in dry pyridine, dimethoxytritylchloride (1.2 eq) was added and the reaction mixture was left under anhydrous conditions overnight. The reaction was quenched with methanol (20 mL), evaporated, dissolved in chloroform, washed with 5% aq. sodium bicarbonate and brine. The organic layer was dried over sodium sulfate and evaporated. The residue was purified by flash chromatography on silica gel, EtOAc:hexanes/1:1 as eluent, to give 0.85 g (57%) of 9 as a white foam.

Example 7

5'-O-Dimethoxytrityl-2'-C-Allyl-Uridine 3'-(2-Cyanoethyl N,N-diisopropylphosphoramidite) (10)

5'-O-Dimethoxytrityl-2'-C-allyl-uridine (0.64 g, 1.12 mmol) was dissolved in dry dichloromethane under dry argon. N,N-Diisopropylethylamine (0.39 mL, 2.24 mmol) was added and the solution was ice-cooled. 2-Cyanoethyl N,N-diisopropylchlorophosphoramidite (0.35 mL, 1.57 mmol) was added dropwise to the stirred reaction solution and stirring was continued for 2 h at RT. The reaction mixture was then ice-cooled and quenched with 12 mL of dry methanol. After stirring for 5 m, the mixture was concentrated in vacuo (40° C.) and purified by flash chromatography on silica gel using a gradient of 10–60% EtOAc in hexanes containing 1% triethylamine mixture as eluent. Yield: 0.78 g (90%), white foam.

Example 8

3',5'-O-(Tetraisopropyl-disiloxane-1,3-diyl)-2'-C-Allyl-$N^4$-Acetyl-Cytidine (11)

Triethylamine (6.35 mL, 45.55 mmol) was added dropwise to a stirred ice-cooled mixture of 1,2,4-triazole (5.66 g, 81.99 mmol) and phosphorous oxychloride (0.86 mL, 9.11 mmol) in 50 mL of anhydrous acetonitrile. To the resulting suspension a solution of 3',5'-O-(tetraisopropyl-disiloxane-1,3-diyl)-2'-C-allyl uridine (2.32 g, 4.55 mmol) in 30 mL of acetonitrile was added dropwise and the reaction mixture was stirred for 4 h at room temperature. The reaction was concentrated in vacuo to a minimal volume (not to dryness). The residue was dissolved in chloroform and washed with water, saturated aq. sodium bicarbonate and brine. The organic layer was dried over sodium sulfate and the solvent was removed in vacuo. The resulting foam was dissolved in 50 mL of 1,4-dioxane and treated with 29% aq. $NH_4OH$ overnight at room temperature. TLC (chloroform:methanol/ 9:1) showed complete conversion of the starting material. The solution was evaporated, dried by coevaporation with anhydrous pyridine and acetylated with acetic anhydride (0.52 mL, 5.46 mmol) in pyridine overnight. The reaction mixture was quenched with methanol, evaporated, the residue was dissolved in chloroform, washed with sodium bicarbonate and brine. The organic layer was dried over sodium sulfate, evaporated to dryness and purified by flash chromatography on silica gel (3% MeOH in chloroform). Yield 2.3 g (90%) as a white foam.

Example 9

5'-O-Dimethoxytrityl-2'- C-Allyl-$N^4$-Acetyl-Cytidine

This compound was obtained analogously to the uridine derivative 9 in 55% yield.

Example 10

5'-O-Dimethoxytrityl-2'-C-allyl-$N^4$-Acetyl-Cytidine 3'-(2-Cyanoethyl N,N-diisopropylphosphoramidite) (12)

2'-O-Dimethoxytrityl-2'-C-allyl-$N^4$-acetyl cytidine (0.8 g, 1.31 mmol) was dissolved in dry dichloromethane under argon. N,N-Diisopropylethylamine (0.46 mL, 2.62 mmol) was added and the solution was ice-cooled. 2-Cyanoethyl N,N-diisopropylchlorophosphoramidite (0.38 mL, 1.7 mmol) was added dropwise to a stirred reaction solution and stirring was continued for 2 h at room temperature. The reaction mixture was then ice-cooled and quenched with 12 mL of dry methanol. After stirring for 5 m, the mixture was concentrated in vacuo (40° C.) and purified by flash chromatography on silica gel using chloroform:ethanol/98:2 with 2% triethylamine mixture as eluent. Yield: 0.91 g (85%), white foam.

Example 11

2'-Deoxy-2'-Methylene-Uridine

2'-Deoxy-2'-methylene-3',5'-O-(tetraisopropyldisiloxane-1,3-diyl)-uridine 14 (Hansske, F.; Madej, D.; Robins, M. J. *Tetrahedron* 1984, 40, 125 and Matsuda, A.; Takenuki, K.; Tanaka, S.; Sasaki, T.; Ueda, T. *J. Med. Chem.* 1991, 34, 812) (2.2 g, 4.55 mmol ) dissolved in THF (20 mL) was treated with 1 M TBAF in THF (10 mL) for 20 m and concentrated in vacuo. The residue was triturated with petroleum ether and chromatographed on a silica gel column. 2'-Deoxy-2'-methylene-uridine (1.0 g, 3.3 mmol, 72.5%) was eluted with 20% MeOH in $CH_2Cl_2$.

Example 12

5'-O-DMT-2'-Deoxy-2'-Methylene-Uridine (15)

2'-Deoxy-2'-methylene-uridine (0.91 g, 3.79 mmol) was dissolved in pyridine (10 mL) and a solution of DMT-Cl in pyridine (10 mL) was added dropwise over 15 m. The resulting mixture was stirred at RT for 12 h and MeOH (2 mL) was added to quench the reaction. The mixture was concentrated in vacuo and the residue taken up in $CH_2Cl_2$ (100 mL) and washed with sat. $NaHCO_3$, water and brine. The organic extracts were dried over $MgSO_4$, concentrated in vacuo and purified over a silica gel column using EtOAc:hexanes as eluant to yield 15 (0.43 g, 0.79 mmol, 22%).

Example 13

5'-O-DMT-2'-Deoxy-2'-Methylene-Uridine 3'-(2-Cyanoethyl N,N-diisopropylphosphoramidite) (17)

1-(2'-Deoxy-2'-methylene-5'-O-dimethoxytrityl-β-D-ribofuranosyl)-uracil (0.43 g, 0.8 mmol) dissolved in dry $CH_2Cl_2$(15 mL) was placed in a round-bottom flask under Ar. Diisopropylethylamine (0.28 mL, 1.6 mmol) was added, followed by the dropwise addition of 2-cyanoethyl N,N-diisopropylchlorophosphoramidite (0.25 mL, 1.12 mmol). The reaction mixture was stirred 2 h at RT and quenched with ethanol (1 mL). After 10 m the mixture evaporated to a syrup in vacuo (40° C.). The product (0.3 g, 0.4 mmol, 50%) was purified by flash column chromatography over silica gel using a 25–70% EtOAc gradient in hexanes, containing 1% triethylamine, as eluant. $R_f$ 0.42 ($CH_2Cl_2$:MeOH/15:1)

Example 14

2'-Deoxy-2'-Difluoromethylene-3',5'-O-(Tetraisopropyldisiloxane-1,3-diyl)-Uridine 2'-Keto-3',5'-O-(tetraisopropyldisiloxane-1,3-diyl)uridine 14(1.92 g, 12.6 mmol) and triphenylphosphine (2.5 g, 9.25 mmol) were dissolved in diglyme (20 mL), and heated to a bath temperature of 160° C. A warm (60° C.) solution of sodium chlorodifluoroacetate in diglyme (50 mL) was added (dropwise from an equilibrating dropping funnel) over a period of ~1 h. The resulting mixture was further stirred for 2 h and concentrated in vacuo. The residue was dissolved in $CH_2Cl_2$and chromatographed over silica gel. 2'-Deoxy-2'-difluoromethylene-3',5'-O-(tetraisopropyldisiloxane-1,3-diyl)-uridine (3.1 g, 5.9 mmol, 70%) eluted with 25% hexanes in EtOAc.

Example 15

2'-Deoxy-2'-Difluoromethylene-Uridine

2'-Deoxy-2'-methylene-3',5'-O-(tetraisopropyldisiloxane-1,3-diyl)-uridine (3.1 g, 5.9 mmol) dissolved in THF (20 mL) was treated with 1M TBAF in THF (10 mL) for 20 m and concentrated in vacuo. The residue was triturated with petroleum ether and chromatographed on silica gel column. 2'-Deoxy-2'-difluoromethylene-uridine (1.1 g, 4.0 mmol, 68%) was eluted with 20% MeOH in CH$_2$Cl$_2$.

Example 16

5'-O-DMT-2'-Deoxy-2'-Difluoromethylene-Uridine (16)

2'-Deoxy-2'-difluoromethylene-uridine (1.1 g, 4.0 mmol) was dissolved in pyridine (10 mL) and a solution of DMT-Cl (1.42 g, 4.18 mmol) in pyridine (10 mL) was added dropwise over 15 m. The resulting mixture was stirred at RT for 12 h and MeOH (2 mL) was added to quench the reaction. The mixture was concentrated in vacuo and the residue taken up in CH$_2$Cl$_2$ (100 mL) and washed with sat. NaHCO$_3$, water and brine. The organic extracts were dried over MgSO$_4$, concentrated in vacuo and purified over a silica gel column using 40% EtOAc:hexanes as eluant to yield 5'-O-DMT-2'-deoxy-2'-difluoromethylene-uridine 16 (1.05 g, 1.8 mmol, 45%).

Example 17

5'-O-DMT-2'-Deoxy-2'-Difluoromethylene-Uridine 3'-(2-Cyanoethyl N,N-diisopropylphosphoramidite) (18)

1-(2'-Deoxy-2'-difluoromethylene-5'-O-dimethoxytrityl-β-D-ribofuranosyl)-uracil (0.577 g, 1 mmol) dissolved in dry CH$_2$Cl$_2$ (15 mL) was placed in a round-bottom flask under Ar. Diisopropylethylamine (0.36 mL, 2 mmol) was added, followed by the dropwise addition of 2-cyanoethyl N,N-diisopropylchlorophosphoramidite (0.44 mL, 1.4 mmol). The reaction mixture was stirred for 2 h at RT and quenched with ethanol (1 mL). After 10 m the mixture evaporated to a syrup in vacuo (40° C.). The product (0.404 g, 0.52 mmol, 52%) was purified by flash chromatography over silica gel using 20–50% EtOAc gradient in hexanes, containing 1% triethylamine, as eluant. R$_f$ 0.48 (CH$_2$Cl$_2$:MeOH/15:1).

Example 18

2'-Deoxy-2'-Methylene-3',5'-O-(Tetraisopropyldisiloxane-1,3-diyl)-4-N-Acetyl-Cytidine 20

Triethylamine (4.8 mL, 34 mmol) was added to a solution of POCl$_3$ (0.65 mL, 6.8 mmol) and 1,2,4-triazole (2.1 g, 30.6 mmol) in acetonitrile (20 mL) at 0° C. A solution of 2'-deoxy-2'-methylene-3',5'-O-(tetraisopropyldisiloxane-1,3-diyl) uridine 19 (1.65 g, 3.4 mmol) in acetonitrile (20 mL) was added dropwise to the above reaction mixture and left to stir at room temperature for 4 h. The mixture was concentrated in vacuo, dissolved in CH$_2$Cl$_2$ (2×100 mL) and washed with 5% NaHCO$_3$ (1×100 mL). The organic extracts were dried over Na$_2$SO$_4$ concentrated in vacuo, dissolved in dioxane (10 mL) and aq. ammonia (20 mL). The mixture was stirred for 12 h and concentrated in vacuo. The residue was azeotroped with anhydrous pyridine (2×20 mL). Acetic anhydride (3 mL) was added to the residue dissolved in pyridine, stirred at RT for 4 h and quenched with sat. NaHCO$_3$(5 mL). The mixture was concentrated in vacuo, dissolved in CH$_2$Cl$_2$ (2×100 mL) and washed with 5% NaHCO$_3$ (1×100 mL). The organic extracts were dried over Na$_2$SO$_4$, concentrated in vacuo and the residue chromatographed over silica gel. 2'-Deoxy-2'-methylene-3',5'-O-(tetraisopropyldisiloxane-1,3-diyl)-4-N-acetyl-cytidine 20 (1.3 g, 2.5 mmol, 73%) was eluted with 20% EtOAc in hexanes.

Example 19

1-(2'-Deoxy-2'-Methylene-5'-O-Dimethoxytrityl-β-D-ribofuranosyl)-4-N-Acetyl-Cytosine 21

2'-Deoxy-2'-methylene-3',5'-O-(tetraisopropyldisiloxane-1,3-diyl)-4-N-acetyl-cytidine 20 (1.3 g, 2.5 mmol) dissolved in THF (20 mL) was treated with 1 M TBAF in THF (3 mL) for 20 m and concentrated in vacuo. The residue was triturated with petroleum ether and chromatographed on silica gel column. 2'-Deoxy-2'-methylene-4-N-acetyl-cytidine (0.56 g, 1.99 mmol, 80%) was eluted with 10% MeOH in CH$_2$Cl$_2$. 2'-Deoxy-2'-methylene-4-N-acetyl-cytidine (0.56 g, 1.99 mmol) was dissolved in pyridine (10 mL) and a solution of DMT-Cl (0.81 g, 2.4 mmol) in pyridine (10 mL) was added dropwise over 15 m. The resulting mixture was stirred at RT for 12 h and MeOH (2 mL) was added to quench the reaction. The mixture was concentrated in vacuo and the residue taken up in CH$_2$Cl$_2$ (100 mL) and washed with sat. NaHCO$_3$(50 mL), water (50 mL) and brine (50 mL). The organic extracts were dried over MgSO$_4$, concentrated in vacuo and purified over a silica gel column using EtOAc:hexanes/60:40 as eluant to yield 21 (0.88 g, 1.5 mmol, 75%).

Example 20

1-(2'-Deoxy-2'-Methylene-5'-O-Dimethoxytriltyl-β-D-ribofuranosyl)-4-N-Acetyl-Cytosine 3'-(2-Cyanoethyl-N,N-diisopropylphosphoramidite) (22)

1-(2'-Deoxy-2'-methylene-5'-O-dimethoxytrityl-β-D-ribofuranosyl)-4-N-acetyl-cytosine 21 (0.88 g, 1.5 mmol) dissolved in dry CH$_2$Cl$_2$(10 mL) was placed in a round-bottom flask under Ar. Diisopropylethylamine (0.8 mL, 4.5 mmol) was added, followed by the dropwise addition of 2-cyanoethyl N,N-diisopropylchlorophosphoramidite (0.4 mL, 1.8 mmol). The reaction mixture was stirred 2 h at room temperature and quenched with ethanol (1 mL). After 10 m the mixture evaporated to a syrup in vacuo (40° C.). The product 22 (0.82 g, 1.04 mmol, 69%) was purified by flash chromatography over silica gel using 50–70% EtOAc gradient in hexanes, containing 1% triethylamine, as eluant. R$_f$ 0.36(CH$_2$Cl$_2$:MeOH/20:1).

Example 21

2'-Deoxy-2'-Difluoromethylene-3',5'-O-(Tetraisopropyl disiloxane-1,3-diyl)-4-N-Acetyl-Cytidine (24)

Et$_3$N (6.9 mL, 50 mmol) was added to a solution of POCl$_3$(0.94 mL, 10 mmol) and 1,2,4-triazole (3.1 g, 45 mmol) in acetonitrile (20 mL) at 0° C. A solution of 2'-deoxy-2'-difluoromethylene-3',5'-O-(tetraisopropyldisiloxane-1,3-diyl)uridine 23([described in example 14] 2.6 g, 5 mmol) in acetonitrile (20 mL) was added dropwise to the above reaction mixture and left to stir at RT for 4 h. The mixture was concentrated in vacuo, dissolved in CH$_2$Cl$_2$(2×100 mL) and washed with 5% NaHCO$_3$(1×100 mL). The organic extracts were dried over Na$_2$SO$_4$ concentrated in vacuo, dissolved in dioxane (20 mL) and aq. ammonia (30 mL). The mixture was stirred for 12 h and concentrated in vacuo. The residue was azeotroped with anhydrous pyridine (2×20 mL). Acetic anhydride (5 mL) was added to the residue dissolved in pyridine, stirred at RT for 4 h and quenched with sat. NaHCO$_3$ (5 mL). The mixture was concentrated in vacuo, dissolved in CH$_2$Cl$_2$ (2×100 mL) and washed with 5% NaHCO$_3$ (1×100 mL).

The organic extracts were dried over Na₂SO₄, concentrated in vacuo and the residue chromatographed over silica gel. 2'-Deoxy-2'-difluoromethylene-3',5'-O-(tetraisopropyldisiloxane-1,3-diyl)-4-N-acetyl-cytidine 24 (2.2 g, 3.9 mmol, 78%) was eluted with 20% EtOAc in hexanes.

Example 22

1-(2'-Deoxy-2'-Difluoromethylene-5'-O-Dimethoxytrityl-β-D-ribofuranosyl)-4-N-Acetyl-Cytosine (25)

2'-Deoxy-2'-difluoromethylene-3',5'-O-(tetraisopropyldisiloxane-1,3-diyl)-4-N-acetyl-cytidine 24 (2.2 g, 3.9 mmol) dissolved in THF (20 mL) was treated with 1 M TBAF in THF (3 mL) for 20 m and concentrated in vacuo. The residue was triturated with petroleum ether and chromatographed on a silica gel column. 2'-Deoxy-2'-difluoromethylene-4-N-acetyl-cytidine (0.89 g, 2.8 mmol, 72%) was eluted with 10% MeOH in CH₂Cl₂. 2'-Deoxy-2'-difluoromethylene-4-N-acetyl-cytidine (0.89 g, 2.8 mmol) was dissolved in pyridine (10 mL) and a solution of DMT-Cl (1.03 g, 3.1 mmol) in pyridine (10 mL) was added dropwise over 15 m. The resulting mixture was stirred at RT for 12 h and MeOH (2 mL) was added to quench the reaction. The mixture was concentrated in vacuo and the residue taken up in CH₂Cl₂ (100 mL) and washed with sat. NaHCO₃ (50 mL), water (50 mL) and brine (50 mL). The organic extracts were dried over MgSO₄, concentrated in vacuo and purified over a silica gel column using EtOAc:hexanes/160:40 as eluant to yield 25 (1.2 g, 1.9 mmol, 68%).

Example 23

1-(2'-Deoxy-2'-Difluoromethylene-5'-O-Dimethoxytrityl-β-D-ribofuranosyl)-4-N-Acetylcytosine 3'-(2-cyanoethyl-N,N-diisopropylphosphoramidite) (26)

1-(2'-Deoxy-2'-difluoromethylene-5'-O-dimethoxytrityl-β-D-ribofuranosyl)-4-N-acetylcytosine 25 (0.6 g, 0.97 mmol) dissolved in dry CH₂Cl₂ (10 mL) was placed in a round-bottom flask under Ar. Diisopropylethylamine (0.5 mL, 2.9 mmol) was added, followed by the dropwise addition of 2-cyanoethyl N,N-diisopropylchlorophosphoramidite (0.4 mL, 1.8 mmol). The reaction mixture was stirred 2 h at RT and quenched with ethanol (1 mL). After 10 m the mixture was evaporated to a syrup in vacuo (40° C.). The product 26, a white foam (0.52 g, 0.63 mmol, 65%) was purified by flash chromatography over silica gel using 30–70% EtOAc gradient in hexanes, containing 1% triethylamine, as eluant. $R_f$ 0.48 (CH₂Cl₂:MeOH/20:1).

Example 24

2'-Keto-3',5'-O-(Tetraisopropyldisiloxane-1,3-diyl)-6-N-(4-t-Butylbenzoyl)-Adenosine (28)

Acetic anhydride (4.6 mL) was added to a solution of 3',5'-O-(tetraisopropyldisiloxane-1,3-diyl)-6-N-(4-t-butylbenzoyl)-adenosine (Brown, J.; Christodolou, C.; Jones, S.; Modak, A.; Reese, C.; Sibanda, S.; Ubasawa A. *J. Chem.Soc. Perkin Trans./*1989, 1735) (6.2 g, 9.2 mmol) in DMSO (37 mL) and the resulting mixture was stirred at room temperature for 24 h. The mixture was concentrated in vacuo. The residue was taken up in EtOAc and washed with water. The organic layer was dried over MgSO₄ and concentrated in vacuo. The residue was purified on a silica gel column to yield 2'-keto-3',5'-O-(tetraisopropyldisiloxane-1,3-diyl)-6-N-(4-t-butylbenzoyl)-adenosine 28 (4.8 g, 7.2 mmol, 78%).

Example 25

2'-Deoxy-2'-methylene-3',5'-O-(Tetraisopropyldisiloxane-1,3-diyl)-6-N-(4-t-Butylbenzoyl)-Adenosine (29)

Under a pressure of argon, sec-butyllithium in hexanes (11.2 mL, 14.6 mmol) was added to a suspension of triphenylmethylphosphonium iodide (7.07 g,17.5 mmol) in THF (25 mL) cooled at −78° C. The homogeneous orange solution was allowed to warm to −30° C. and a solution of 2'-keto-3',5'-O-(tetraisopropyldisiloxane-1,3-diyl)-6-N-(4-t-butylbenzoyl)-adenosine 28 (4.87 g, 7.3 mmol) in THF (25 mL) was transferred to this mixture under argon pressure. After warming to RT, stirring was continued for 24 h. THF was evaporated and replaced by CH₂Cl₂ (250 mL), water was added (20 mL), and the solution was neutralized with a cooled solution of 2% HCl. The organic layer was washed with H₂O (20 mL), 5% aqueous NaHCO₃ (20 mL), H₂O to neutrality, and brine (10 mL). After drying (Na₂SO₄), the solvent was evaporated in vacuo to give the crude compound, which was chromatographed on a silica gel column. Elution with light petroleum ether:EtOAc/7:3 afforded pure 2'-deoxy-2'-methylene-3',5'-O-(tetraisopropyldisiloxane-1,3-diyl)-6-N-(4-t-butylbenzoyl)-adenosine 29 (3.86 g, 5.8 mmol, 79%).

Example 26

2'-Deoxy-2'-Methylene-6-N-(4-t-Butylbenzoyl)-Adenosine

2'-deoxy-2'-methylene-3',5'-O-(tetraisopropyldisiloxane-1,3-diyl)-6-N-(4-t-butylbenzoyl)-adenosine (3.86 g, 5.8 mmol) dissolved in THF (30 mL) was treated with 1M TBAF in THF (15 mL) for 20 m and concentrated in vacuo. The residue was triturated with petroleum ether and chromatographed on a silica gel column. 2'-Deoxy-2'-methylene-6-N-(4-t-butylbenzoyl)-adenosine (1.8 g, 4.3 mmol, 74%) was eluted with 10% MeOH in CH₂Cl₂.

Example 27

5'-O-DMT-2'-Deoxy-2'-Methylene-6-N-(4-t-Butylbenzoyl)-Adenosine (29)

2'-Deoxy-2'-methylene-6-N-(4-t-butylbenzoyl)-adenosine (0.75 g, 1.77 mmol) was dissolved in pyridine (10 mL) and a solution of DMT-Cl (0.66 g, 1.98 mmol) in pyridine (10 mL) was added dropwise over 15 m. The resulting mixture was stirred at RT for 12 h and MeOH (2 mL) was added to quench the reaction. The mixture was concentrated in vacuo and the residue taken up in CH₂Cl₂ (100 mL) and washed with sat. NaHCO₃, water and brine. The organic extracts were dried over MgSO₄, concentrated in vacuo and purified over a silica gel column using 50% EtOAc:hexanes as an eluant to yield 29 (0.81 g, 1.1 mmol, 62%).

Example 28

5'-O-DMT-2'-Deoxy-2'-Methylene-6-N-(4-t-Butylbenzoyl)-Adenosine 3'-(2-Cyanoethyl N,N-diisopropylphosphoramidite) (31)

1-(2'-Deoxy-2'-methylene-5'-O-dimethoxytrityl-β-D-ribofuranosyl)-6-N-(4-t-butylbenzoyl)-adenine 29 dissolved in dry CH$_2$Cl$_2$ (15 mL) was placed in a round bottom flask under Ar. Diisopropylethylamine was added, followed by the dropwise addition of 2-cyanoethyl N,N-diisopropylchlorophosphoramidite. The reaction mixture was stirred 2 h at RT and quenched with ethanol (1 mL). After 10 m the mixture was evaporated to a syrup in vacuo (40° C.). The product was purified by flash chromatography over silica gel using 30–50% EtOAc gradient in hexanes, containing 1% triethylamine, as eluant (0.7 g, 0.76 mmol, 68%). R$_f$ 0.45 (CH$_2$Cl$_2$:MeOH/20:1)

Example 29

2'-Deoxy-2'-Difluoromethylene-3',5'-O-(Tetraisopropyldisiloxane-1,3-diyl)-6-N-(4- t-Butylbenzoyl)-Adenosine 2'-Keto-3',5'-O-(tetraisopropyldisiloxane-1,3-diyl)-6-N-(4-t-butyl-benzoyl)-adenosine 28 (6.7 g, 10 mmol) and triphenylphosphine (2.9 g, 11 mmol) were dissolved in diglyme (20 mL), and heated to a bath temperature of 160° C. A warm (60° C.) solution of sodium chlorodifluoroacetate (2.3 g, 15 mmol) in diglyme (50 mL) was added (dropwise from an equilibrating dropping funnel) over a period of ~1 h. The resulting mixture was further stirred for 2 h and concentrated in vacuo. The residue was dissolved in CH$_2$Cl$_2$ and chromatographed over silica gel. 2'-Deoxy-2'-difluoromethylene-3',5'-O-(tetraisopropyldisiloxane-1,3-diyl)-6-N-(4-t-butylbenzoyl)-adenosine (4.1 g, 6.4 mmol, 64%) eluted with 15% hexanes in EtOAc.

Example 30

2'-Deoxy-2'-Difluoromethylene-6-N-(4-t-Butylbenzoyl)-Adenosine

2'-Deoxy-2'-difluoromethylene-3',5'-O-(tetraisopropyldisiloxane-1,3-diyl)-6-N-(4-t-butylbenzoyl)-adenosine (4.1 g, 6.4 mmol) dissolved in THF (20 mL) was treated with 1M TBAF in THF (10 mL) for 20 m and concentrated in vacuo. The residue was triturated with petroleum ether and chromatographed on a silica gel column. 2'-Deoxy-2'-difluoromethylene-6-N-(4-t-butylbenzoyl)-adenosine (2.3 g, 4.9 mmol, 77%) was eluted with 20% MeOH in CH$_2$Cl$_2$.

Example 31

5'-O-DMT-2'-Deoxy-2'-Difluoromethylene-6-N-(4-t-Butylbenzoyl)-Adenosine (30)

2'-Deoxy-2'-difluoromethylene-6-N-(4-t-butylbenzoyl)-adenosine (2.3 g, 4.9 mmol) was dissolved in pyridine (10 mL) and a solution of DMT-Cl in pyridine (10 mL) was added dropwise over 15 m. The resulting mixture was stirred at RT for 12 h and MeOH (2 mL) was added to quench the reaction. The mixture was concentrated in vacuo and the residue taken up in CH$_2$Cl$_2$ (100 mL) and washed with sat. NaHCO$_3$, water and brine. The organic extracts were dried over MgSO$_4$, concentrated in vacuo and purified over a silica gel column using 50% EtOAc:hexanes as eluant to yield 30 (2.6 g, 3.41 mmol, 69%).

Example 32

5'-O-DMT-2'-Deoxy-2'-Difluoromethylene-6-N-(4-t-Butylbenzoyl)-Adenosine 3'-(2-Cyanoethyl N,N-diisopropylphosphoramidite) (32)

1-(2'-Deoxy-2'-difluoromethylene-5'-O-dimethoxytrityl-β-D-ribofuranosyl)-6-N-(4-t-butylbenzoyl)-adenine 30(2.6 g, 3.4 mmol) dissolved in dry CH$_2$Cl$_2$(25 mL) was placed in a round bottom flask under Ar. Diisopropylethylamine (1.2 mL, 6.8 mmol) was added, followed by the dropwise addition of 2-cyanoethyl N,N-diisopropylchlorophosphoramidite (1.06 mL, 4.76 mmol). The reaction mixture was stirred 2 h at RT and quenched with ethanol (1 mL). After 10 m the mixture evaporated to a syrup in vacuo (40° C.). 32 (2.3 g, 2.4 mmol, 70%) was purified by flash column chromatography over silica gel using 20–50% EtOAc gradient in hexanes, containing 1% triethylamine, as eluant. R$_f$ 0.52 (CH$_2$Cl$_2$:MeOH/15:1).

Example 33

2'-Deoxy-2'-Methoxycarbonylmethylidine-3',5'-O-(Tetraisopropyldisiloxane-1,3-diyl)-Uridine (33)

Methyl(triphenylphosphoranylidine)acetate (5.4 g, 16 mmol) was added to a solution of 2'-keto-3',5'-O-(tetraisopropyl disiloxane-1,3-diyl)-uridine 14 in CH$_2$Cl$_2$ under argon. The mixture was left to stir at RT for 30 h. CH$_2$Cl$_2$ (100 mL) and water were added (20 mL), and the solution was neutralized with a cooled solution of 2% HCl. The organic layer was washed with H$_2$O (20 mL), 5% aq. NaHCO$_3$(20 mL), H$_2$O to neutrality, and brine (10 mL). After drying (Na$_2$SO$_4$), the solvent was evaporated in vacuo to give crude product, that was chromatographed on a silica gel column. Elution with light petroleum ether:EtOAc/7:3 afforded pure 2'-deoxy-2'-methoxycarbonylmethylidine-3',5'-O-(tetraisopropyldisiloxane-1,3-diyl)-uridine 33 (5.8 g, 10.8 mmol, 67.5%).

Example 34

2'-Deoxy-2'-Methoxycarbonylmethylidine-Uridine (34)

Et$_3$N.3 HF (3 mL) was added to a solution of 2'-deoxy-2'-methoxycarboxylmethylidine-3',5'-O-(tetraisopropyldisiloxane-1,3-diyl)-uridine 33 (5 g, 9.3 mmol) dissolved in CH$_2$Cl$_2$ (20 mL) and Et$_3$N (15 mL). The resulting mixture was evaporated in vacuo after 1 h and chromatographed on a silica gel column eluting 2'-deoxy-2'-methoxycarbonylmethylidine-uridine 34 (2.4 g, 8 mmol, 86%) with THF:CH$_2$Cl$_2$/4:1.

Example 35

5'-O-DMT-2'-Deoxy-2'-Methoxycarbonylmethylidine-Uridine (35)

2'-Deoxy-2'-methoxycarbonylmethylidine-uridine 34 (1.2 g, 4.02 mmol) was dissolved in pyridine (20 mL). A solution of DMT-Cl (1.5 g, 4.42 mmol) in pyridine (10 mL) was added dropwise over 15 m. The resulting mixture was stirred at RT for 12 h and MeOH (2 mL) was added to quench the reaction. The mixture was concentrated in vacuo and the residue taken up in CH$_2$Cl$_2$ (100 mL) and washed with sat. NaHCO$_3$, water and brine. The organic extracts were dried over MgSO$_4$, concentrated in vacuo and purified over a silica gel column using 2–5% MeOH in CH$_2$Cl$_2$ as an eluant to yield 5'-O-DMT-2'-deoxy-2'-methoxycarbonylmethylidine-uridine 35 (2.03 g, 3.46 mmol, 86%).

Example 36

5'-O-DMT-2'-Deoxy-2'-Methoxycarbonylmethylidine-Uridine 3'-(2-cyanoethyl-N,N-diisopropylphosphoramidite) (36)

1-(2'- Deoxy-2'-methoxycarbonylmethylidine-5'-O-dimethoxytrityl-β-D-ribofuranosyl)-uridine 35 (2.0 g, 3.4 mmol) dissolved in dry $CH_2Cl_2$ (10 mL) was placed in a round-bottom flask under Ar. Diisopropylethylamine (1.2 mL, 6.8 mmol) was added, followed by the dropwise addition of 2-cyanoethyl N,N-diisopropylchlorophosphoramidite (0.91 mL, 4.08 mmol). The reaction mixture was stirred 2 h at RT and quenched with ethanol (1 mL). After 10 m the mixture was evaporated to a syrup in vacuo (40° C.). 5'-O-DMT-2'-deoxy-2'-methoxycarbonylmethylidine-uridine 3'-(2-cyanoethyl-N,N-diisopropylphosphoramidite) 36 (1.8 g, 2.3 mmol, 67%) was purified by flash column chromatography over silica gel using a 30–60% EtOAc gradient in hexanes, containing 1% triethylamine, as eluant. $R_f$ 0.44 ($CH_2Cl_2$:MeOH/9.5:0.5).

Example 37

2'-Deoxy-2'-Carboxymethylidine-3',5'-O-(Tetraisopropyldisiloxane-1,3-diyl)-Uridine 37

2'-Deoxy-2'-methoxycarbonylmethylidine-3',5'-O-(tetraisopropyldisiloxane-1,3-diyl)-uridine 33 (5.0 g, 10.8 mmol) was dissolved in MeOH (50 mL) and 1N NaOH solution (50 mL) was added to the stirred solution at RT. The mixture was stirred for 2 h and MeOH removed in vacuo. The pH of the aqueous layer was adjusted to 4.5 with 1N HCl solution, extracted with EtOAc (2×100 mL), washed with brine, dried over $MgSO_4$ and concentrated in vacuo to yield the crude acid. 2'-Deoxy-2'-carboxymethylidine- 3',5'-O-(tetraisopropyldisiloxane-1,3-diyl)-uridine 37 (4.2 g, 7.8 mmol, 73%) was purified on a silica gel column using a gradient of 10–15% MeOH in $CH_2Cl_2$.

Uses

The alkyl substituted nucleotides of this invention can be used to form stable oligonucleotides as discussed above for use in enzymatic cleavage or antisense situations. Such oligonucleotides can be formed enzymatically using triphosphate forms by standard procedure. Administration of such oligonucleotides is by standard procedure. See Draper et al. PCT WO 94/(198/063).

Other embodiments are within the following claims.

We claim:

1. An enzymatic nucleic acid molecule comprising a 2'-deoxy-2'-alkylnucleotide, wherein said enzymatic nucleic acid molecule is capable of cleaving a separate RNA molecule.

2. The enzymatic nucleic acid molecule of claim 1, wherein said enzymatic nucleic acid molecule comprises ribonucleotides.

3. The enzymatic nucleic acid molecule of claim 1, wherein said enzymatic nucleic acid molecule comprises deoxyribonucleotides.

4. The enzymatic nucleic acid molecule of claim 1, wherein said enzymatic nucleic acid molecule comprises 2'-O-methylnucleotides.

5. The enzymatic nucleic acid molecule of claim 1, wherein said 2'-deoxy-2'-alkyl nucleotide is 2'-deoxy-2'-allyl nucleotide.

6. The enzymatic nucleic acid molecule of claim 1, wherein said enzymatic nucleic acid molecule comprises a catalytic core region and a substrate binding region, wherein said catalytic core region comprises said 2'-deoxy-2'-alkyl nucleotide.

7. The enzymatic nucleic acid molecule of claim 1, wherein said enzymatic nucleic acid molecule comprises a catalytic core region and a substrate binding region, wherein said substrate binding region comprises said 2'-deoxy-2'-alkyl nucleotide.

8. The enzymatic nucleic acid molecule of claim 1, wherein said enzymatic nucleic acid molecule cleaves said separate RNA molecule in the presence of a divalent cation.

9. The enzymatic nucleic acid molecule of claim 1, wherein said divalent cation is magnesium.

10. A method of cleaving a separate RNA molecule comprising the step of contacting said separate RNA molecule with the enzymatic nucleic acid molecule of claim 1, under conditions suitable for the cleavage of said separate RNA molecule.

11. The method of claim 10, wherein said cleavage occurs in the presence of a divalent cation.

12. The method of claim 11, wherein said divalent cation is magnesium.

* * * * *

SEQUENCE LISTING (1) GENERAL INFORMATION:

(iii) NUMBER OF SEQUENCES: 6

(2) INFORMATION FOR SEQ ID NO: 1:

(i) SEQUENCE CHARACTERISTICS:
      (A) LENGTH:         11
      (B) TYPE:            nucleic acid
      (C) STRANDEDNESS:   single
      (D) TOPOLOGY:       linear (ix) FEATURE:
      (D) OTHER INFORMATION:   The letter "N"
         stands for any base.
         "H" represents
         nucleotide C, A, or
         U.

(ii) SEQUENCE DESCRIPTION: SEQ ID NO: 1:

NNNNUHNNNN N                            11

(2) INFORMATION FOR SEQ ID NO: 2:

(i) SEQUENCE CHARACTERISTICS:
      (A) LENGTH:         32
      (B) TYPE:            nucleic acid
      (C) STRANDEDNESS:   single
      (D) TOPOLOGY:       linear (ix) FEATURE:
      (D) OTHER INFORMATION:   The letter "N"
         stands for any base.

(ii) SEQUENCE DESCRIPTION: SEQ ID NO: 2:

NNNNNCUGAN GAGNNNNNNN NNNCGAAANN NN        32

(2) INFORMATION FOR SEQ ID NO: 3:

(i) SEQUENCE CHARACTERISTICS:
      (A) LENGTH:         14
      (B) TYPE:            nucleic acid
      (C) STRANDEDNESS:   single
      (D) TOPOLOGY:       linear (ix) FEATURE:
      (D) OTHER INFORMATION:   The letter "N"

-continued stands for any base.

(ii) SEQUENCE DESCRIPTION: SEQ ID NO: 3:

NNNNNGUCNN NNNN                                                                    14

(2) INFORMATION FOR SEQ ID NO: 4:

(i) SEQUENCE CHARACTERISTICS:
      (A) LENGTH:           50
      (B) TYPE:             nucleic acid
      (C) STRANDEDNESS:     single
      (D) TOPOLOGY:         linear (ix) FEATURE:
       (D) OTHER INFORMATION:   The letter "N"
           stands for any base.

(ii) SEQUENCE DESCRIPTION: SEQ ID NO: 4:

NNNNNNAGAA NNNNACCAGA GAAACACACG UUGUGGUAUA UUACCUGGUA                              50

(2) INFORMATION FOR SEQ ID NO: 5:

(i) SEQUENCE CHARACTERISTICS:
      (A) LENGTH:           85
      (B) TYPE:             nucleic acid
      (C) STRANDEDNESS:     single
      (D) TOPOLOGY:         linear (ii) SEQUENCE DESCRIPTION: SEQ ID NO: 5:

UGGCCGGCAU GGUCCCAGCC UCCUCGCUGG CGCCGGCUGG GCAACAUUCC                              50

GAGGGGACCG UCCCCUCGGU AAUGGCGAAU GGGAC                                              85

(2) INFORMATION FOR SEQ ID NO: 6:

(i) SEQUENCE CHARACTERISTICS:
      (A) LENGTH:           35
      (B) TYPE:             nucleic acid
      (C) STRANDEDNESS:     single
      (D) TOPOLOGY:         linear (ii) SEQUENCE DESCRIPTION: SEQ ID NO: 6:

UCCCUAAAAG CCGGAAAGCC GAGUAGUCUA CCUCU                                              35